(12) United States Patent
Schlievert et al.

(10) Patent No.: US 9,789,176 B2
(45) Date of Patent: Oct. 17, 2017

(54) **COMPOSITIONS AND METHODS FOR INDUCING IMMUNE RESPONSES AGAINST BACTERIA IN THE GENUS *STAPHYLOCOCCUS***

(75) Inventors: Patrick M. Schlievert, Iowa City, IA (US); Marnie L. Peterson, Golden Valley, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 129 days.

(21) Appl. No.: 14/005,510

(22) PCT Filed: Mar. 16, 2012

(86) PCT No.: PCT/US2012/029434
§ 371 (c)(1),
(2), (4) Date: Mar. 20, 2014

(87) PCT Pub. No.: WO2012/170097
PCT Pub. Date: Dec. 13, 2012

(65) Prior Publication Data
US 2014/0199339 A1 Jul. 17, 2014

Related U.S. Application Data

(60) Provisional application No. 61/453,216, filed on Mar. 16, 2011.

(51) Int. Cl.
| | | |
|---|---|---|
| *A61K 39/02* | (2006.01) | |
| *A61K 39/09* | (2006.01) | |
| *A61K 45/00* | (2006.01) | |
| *A61K 39/085* | (2006.01) | |
| *C07K 14/315* | (2006.01) | |
| *A61K 39/39* | (2006.01) | |
| *A61K 38/48* | (2006.01) | |
| *A61K 39/00* | (2006.01) | |

(52) U.S. Cl.
CPC ........ *A61K 39/085* (2013.01); *A61K 38/4893* (2013.01); *A61K 39/00* (2013.01); *A61K 39/39* (2013.01); *A61K 2039/55544* (2013.01); *C07K 14/315* (2013.01)

(58) Field of Classification Search
CPC .... A61K 39/00; A61K 38/4893; A61K 39/39; C07K 14/315
See application file for complete search history.

(56) References Cited

U.S. PATENT DOCUMENTS

| | | | |
|---|---|---|---|
| 4,450,150 A | 5/1984 | Sidman | |
| 4,675,381 A | 6/1987 | Bichon | |
| 5,417,986 A | 5/1995 | Reid | |
| 6,391,315 B1 * | 5/2002 | Takahashi | C07K 16/18 424/236.1 |
| 6,399,332 B1 * | 6/2002 | Ulrich et al. | 435/69.3 |
| 2010/0021503 A1 * | 1/2010 | Denoel et al. | 424/243.1 |
| 2010/0322959 A1 * | 12/2010 | Biemans | A61K 39/085 424/194.1 |
| 2013/0230550 A1 * | 9/2013 | Schneewind | A61K 39/085 424/190.1 |
| 2013/0259896 A1 * | 10/2013 | Khandke | A61K 39/085 424/197.11 |

FOREIGN PATENT DOCUMENTS

| | | | |
|---|---|---|---|
| WO | WO 00/02523 | * | 1/2000 |
| WO | WO 2007/145689 | | 12/2007 |
| WO | WO 2009/029831 | | 3/2009 |

OTHER PUBLICATIONS

Otto, Exert Opin Biol Ther., Jul. 2010; 10(7): 1049-1059.*
Malam et al., J. Clin. Pathol., 1992; 45: 716-721.*
Barsumian et al., "Nonspecific and specific immunological mitogenicity by group A streptococcal pyrogenic exotoxins," *Infect Immun.*, 22(3):681-688, Dec. 1978.
Blomster-Hautamaa and Schlievert, "Preparation of toxic shock syndrome toxin-1," *Methods Enzymol.*, 165:37-43, 1988.
Blomster-Hautamaa et al., "Resolution of highly purified toxic-shock syndrome toxin 1 into two distinct proteins by isoelectric focusing," *Biochemistry*, 25(1):54-59, Jan. 14, 1986.
Bubeck Wardenburg and Schneewind, "Vaccine protection against *Staphylococcus aureus* pneumonia," *J Exp Med.*, 205(2):287-294, Feb. 18, 2008.
Daum et al., "A novel methicillin-resistance cassette in community-acquired methicillin-resistant *Staphylococcus aureus* isolates of diverse genetic backgrounds," *J Infect Dis.*, 186(9):1344-1347, Epub Oct. 3, 2002.
Elgueta et al., "Molecular mechanism and function of CD40/CD40L engagement in the immune system," *Immunol Rev.*, 229(1):152-172, May 2009.
Fey et al., "Comparative molecular analysis of community- or hospital-acquired methicillin-resistant *Staphylococcus aureus*," *Antimicrob Agents Chemother.*, 47(1):196-203, Jan. 2003.
From the Centers for Disease Control and Prevention, "Four pediatric deaths from community-acquired methicillin-resistant *Staphylococcus aureus*—Minnesota and North Dakota, 1997-1999," *JAMA*, 282(12):1123-1125, Sep. 22-29, 1999.
From the Centers for Disease Control and Prevention, "Methicillin-resistant *Staphylococcus aureus* infections in correctional facilities—Georgia, California, and Texas, 2001-2003," *MMWR Morb Mortal Wkly Rep.*, 52(41):992-996, Oct. 17, 2003.
Gaskin et al., "Purification of *Staphylococcus aureus* beta-toxin: comparison of three isoelectric focusing methods," *Protein Expr Purif.*, 9(1):76-82, Feb. 1997.
Huseby et al., "Structure and biological activities of beta toxin from *Staphylococcus aureus*," *J Bacteriol.*, 189(23):8719-8726, Epub Sep. 14, 2007.

(Continued)

*Primary Examiner* — Gary Nickol
*Assistant Examiner* — Lakia Jackson-Tongue
(74) *Attorney, Agent, or Firm* — Fish & Richardson P.C.

(57) ABSTRACT

This disclosure features compositions that include two or more staphylococcal toxoids and are useful for inducing protective immune responses against staphylococcal diseases.

18 Claims, 15 Drawing Sheets

(56) References Cited

OTHER PUBLICATIONS

Jardetzky et al., "Three-dimensional structure of a human class II histocompatibility molecule complexed with superantigen," *Nature*, 368(6473):711-718, Apr. 21, 1994.

Kim et al., "Toxic shock syndrome toxin-1 complexed with a class II major histocompatibility molecule HLA-DR1," *Science*, 266(5192):1870-1874, Dec. 16, 1994.

Klevens et al., "Invasive methicillin-resistant *Staphylococcus aureus* infections in the United States," *JAMA.*, 298(15):1763-1771, Oct. 17, 2007.

Leder et al., "A mutational analysis of the binding of staphylococcal enterotoxins B and C3 to the T cell receptor beta chain and major histocompatibility complex class II," *J Exp Med.*, 187(6):823-833, Mar. 16, 1998.

Lee et al., "Fluid replacement protection of rabbits challenged subcutaneous with toxic shock syndrome toxins," *Infect Immun.*, 59(3):879-884, Mar. 1991.

Lin et al., "Proinflammatory exoprotein characterization of toxic shock syndrome *Staphylococcus aureus*," *Biochemistry*, 50(33):7157-7167, Epub Jul. 21, 2011.

Lowy, "*Staphylococcus aureus* infections," *N Engl J Med* 339(8):520-532, Aug. 1998.

MacDonald et al., "Toxic shock syndrome. A newly recognized complication of influenza and influenzalike illness," *JAMA*, 257(8):1053-1058, Feb. 27, 1987.

Marrack and Kappler, "The staphylococcal enterotoxins and their relatives," *Science*, 248(4956):705-711, May 11, 1990.

McCormick et al., "Functional analysis of the TCR binding domain of toxic shock syndrome toxin-1 predicts further diversity in MHC class II/superantigen/TCR ternary complexes," *J Immunol.*, 171(3):1385-1392, Aug. 1, 2003.

McCormick et al., "Toxic shock syndrome and bacterial superantigens: an update," *Annu Rev Microbiol.*, 55:77-104, 2001.

Murray et al., "Immunobiologic and biochemical properties of mutants of toxic shock syndrome toxin-1," *J Immunol.*, 152(1):87-95, Jan. 1, 1994.

Murray et al., "Localization of biologically important regions on toxic shock syndrome toxin 1," *Infect Immun.*, 64(1):371-374, Jan. 1996.

Osterholm et al., "Tri-state toxic-state syndrome study. I. Epidemiologic findings," *J Infect Dis.*, 145(4):431-440, Apr. 1982.

Parsonnet et al., "Prevalence of toxic shock syndrome toxin 1-producing *Staphylococcus aureus* and the presence of antibodies to this superantigen in menstruating women," *J Clin Microbiol.*, 43(9):4628-4634, Sep. 2005.

Peterson et al., "The innate immune system is activated by stimulation of vaginal epithelial cells with *Staphylococcus aureus* and toxic shock syndrome toxin 1," *Infect Immun.*, 73(4):2164-2174, Apr. 2005.

Schlievert and Blomster, "Production of staphylococcal pyrogenic exotoxin type C: influence of physical and chemical factors," *J Infect Dis.*, 147(2):236-242, Feb. 1983.

Schlievert et al., "Aggregation and binding substances enhance pathogenicity in rabbit models of Enterococcus faecalis endocarditis," *Infect Immun.*, 66(1):218-223, Jan. 1998.

Schlievert et al., "Identification and characterization of an exotoxin from *Staphylococcus aureus* associated with toxic-shock syndrome," *J Infect Dis.*, 143(4):509-516, Apr. 1981.

Schlievert et al., "Secreted virulence factor comparison between methicillin-resistant and methicillin-sensitive *Staphylococcus aureus*, and its relevance to atopic dermatitis," *J Allergy Clin Immunol.*, 125(1):39-49, Jan. 2010.

Schlievert, "Enhancement of host susceptibility to lethal endotoxin shock by staphylococcal pyrogenic exotoxin type C," *Infect Immun.*, 36(1):123-128, Apr. 1982.

Spaulding et al., "Vaccination Against *Staphylococcus aureus* Pneumonia," *J Infect Dis.*, Epub Dec. 19, 2013, 33 pages.

Strandberg et al., "Staphylococcal superantigens cause lethal pulmonary disease in rabbits," *J Infect Dis.*, 202(11):1690-1697, Epub Oct. 27, 2010.

Stranger-Jones et al., "Vaccine assembly from surface proteins of *Staphylococcus aureus*," *Proc Natl Acad Sci U S A.*, 103(45):16942-16947, Epub Oct. 30, 2006.

Tollersrud et al., "Antibody responses in sheep vaccinated against *Staphylococcus aureus* mastitis: a comparison of two experimental vaccines containing different adjuvants," *Vet Res Commun.*, 26(8):587-600, Dec. 2002.

Vergeront et al., "Prevalence of serum antibody to staphylococcal enterotoxin F among Wisconsin residents: implications for toxic-shock syndrome," *J Infect Dis.*, 148(4):692-698, Oct. 1983.

International Search Report and Written Opinion for PCT/US2012/029434, mailed Feb. 13, 2013, 10 pages.

International Preliminary Report on Patentability for PCT/US2012/029434, mailed Sep. 26, 2013, 8 pages.

* cited by examiner

SEQUENCE LISTING

<160> NUMBER OF SEQ ID NOS: 8

<210> SEQ ID NO 1
<211> LENGTH: 194
<212> TYPE: PRT
<213> ORGANISM: Staphylococcus aureus
<220> FEATURE:
<221> NAME/KEY: MISC_FEATURE
<222> LOCATION: (19)..(19)
<223> OTHER INFORMATION: Thr can be mutated
<220> FEATURE:
<221> NAME/KEY: MISC_FEATURE
<222> LOCATION: (31)..(31)
<223> OTHER INFORMATION: Gly can be mutated to Ser
<220> FEATURE:
<221> NAME/KEY: MISC_FEATURE
<222> LOCATION: (32)..(32)
<223> OTHER INFORMATION: Ser can be mutated to Pro
<220> FEATURE:
<221> NAME/KEY: MISC_FEATURE
<222> LOCATION: (55)..(55)
<223> OTHER INFORMATION: Ala can be mutated
<220> FEATURE:
<221> NAME/KEY: MISC_FEATURE
<222> LOCATION: (57)..(57)
<223> OTHER INFORMATION: Thr can be mutated
<220> FEATURE:
<221> NAME/KEY: MISC_FEATURE
<222> LOCATION: (69)..(69)
<223> OTHER INFORMATION: Thr can be mutated
<220> FEATURE:
<221> NAME/KEY: MISC_FEATURE
<222> LOCATION: (80)..(80)
<223> OTHER INFORMATION: Tyr can be mutated
<220> FEATURE:
<221> NAME/KEY: MISC_FEATURE
<222> LOCATION: (132)..(132)
<223> OTHER INFORMATION: Glu can be mutated
<220> FEATURE:
<221> NAME/KEY: MISC_FEATURE
<222> LOCATION: (135)..(135)
<223> OTHER INFORMATION: His can be mutated to Ala
<220> FEATURE:
<221> NAME/KEY: MISC_FEATURE
<222> LOCATION: (136)..(136)
<223> OTHER INFORMATION: Gln can be mutated to Ala
<220> FEATURE:
<221> NAME/KEY: MISC_FEATURE
<222> LOCATION: (139)..(139)
<223> OTHER INFORMATION: Gln can be mutated to Ala
<220> FEATURE:
<221> NAME/KEY: MISC_FEATURE
<222> LOCATION: (140)..(140)
<223> OTHER INFORMATION: Ile can be mutated

<400> SEQUENCE: 1

```
Ser Thr Asn Asp Asn Ile Lys Asp Leu Leu Asp Trp Tyr Ser Ser Gly
1               5                   10                  15

Ser Asp Thr Phe Thr Asn Ser Glu Val Leu Asp Asn Ser Leu Gly Ser
            20                  25                  30

Met Arg Ile Lys Asn Thr Asp Gly Ser Ile Ser Leu Ile Ile Phe Pro
        35                  40                  45

Ser Pro Tyr Tyr Ser Pro Ala Phe Thr Lys Gly Glu Lys Val Asp Leu
    50                  55                  60

Asn Thr Lys Arg Thr Lys Lys Ser Gln His Thr Ser Glu Gly Thr Tyr
65                  70                  75                  80

Ile His Phe Gln Ile Ser Gly Val Thr Asn Thr Glu Lys Leu Pro Thr
                85                  90                  95

Pro Ile Glu Leu Pro Leu Lys Val Lys Val His Gly Lys Asp Ser Pro
            100                 105                 110
```

Leu Lys Tyr Trp Pro Lys Phe Asp Lys Lys Gln Leu Ala Ile Ser Thr
            115                 120                 125

Leu Asp Phe Glu Ile Arg His Gln Leu Thr Gln Ile His Gly Leu Tyr
130                 135                 140

Arg Ser Ser Asp Lys Thr Gly Gly Tyr Trp Lys Ile Thr Met Asn Asp
145                 150                 155                 160

Gly Ser Thr Tyr Gln Ser Asp Leu Ser Lys Lys Phe Glu Tyr Asn Thr
                165                 170                 175

Glu Lys Pro Pro Ile Asn Ile Asp Glu Ile Lys Thr Ile Glu Ala Glu
            180                 185                 190

Ile Asn

<210> SEQ ID NO 2
<211> LENGTH: 239
<212> TYPE: PRT
<213> ORGANISM: Staphylococcus aureus
<220> FEATURE:
<221> NAME/KEY: MISC_FEATURE
<222> LOCATION: (23)..(23)
<223> OTHER INFORMATION: Asn can be mutated to Ala
<220> FEATURE:
<221> NAME/KEY: MISC_FEATURE
<222> LOCATION: (90)..(90)
<223> OTHER INFORMATION: Tyr can be mutated to Ala
<220> FEATURE:
<221> NAME/KEY: MISC_FEATURE
<222> LOCATION: (210)..(210)
<223> OTHER INFORMATION: Gln can be mutated to Ala

<400> SEQUENCE: 2

Glu Ser Gln Pro Asp Pro Met Pro Asp Asp Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Lys Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Asp Leu Ala Lys Lys Tyr Lys Asp Glu
65                  70                  75                  80

Val Val Asp Val Tyr Gly Ser Asn Tyr Tyr Val Asn Cys Tyr Phe Ser
                85                  90                  95

Ser Lys Asp Asn Val Gly Lys Val Thr Gly Gly Lys Thr Cys Met Tyr
            100                 105                 110

Gly Gly Ile Thr Lys His Glu Gly Asn His Phe Asp Asn Gly Asn Leu
        115                 120                 125

Gln Asn Val Leu Val Arg Val Tyr Glu Asn Lys Arg Asn Thr Ile Ser
    130                 135                 140

Phe Glu Val Gln Thr Asp Lys Lys Ser Val Thr Ala Gln Glu Leu Asp
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Trp Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

```
Ser Lys Ser Val Lys Ile Glu Val His Leu Thr Thr Lys Asn Gly
225                 230                 235
```

<210> SEQ ID NO 3
<211> LENGTH: 238
<212> TYPE: PRT
<213> ORGANISM: Staphylococcus aureus
<220> FEATURE:
<221> NAME/KEY: MISC_FEATURE
<222> LOCATION: (20)..(20)
<223> OTHER INFORMATION: Thr can be mutated to Leu
<220> FEATURE:
<221> NAME/KEY: MISC_FEATURE
<222> LOCATION: (26)..(26)
<223> OTHER INFORMATION: Val can be mutated to Tyr
<220> FEATURE:
<221> NAME/KEY: MISC_FEATURE
<222> LOCATION: (90)..(90)
<223> OTHER INFORMATION: Tyr can be mutated to Ala

<400> SEQUENCE: 3

```
Glu Ser Gln Pro Asp Pro Lys Pro Asp Glu Leu His Lys Ser Lys
1               5                   10                  15

Phe Thr Gly Leu Met Glu Asn Met Lys Val Leu Tyr Asp Asp Asn His
                20                  25                  30

Val Ser Ala Ile Asn Val Lys Ser Ile Asp Gln Phe Leu Tyr Phe Asp
                35                  40                  45

Leu Tyr Ser Ile Lys Asp Thr Lys Leu Gly Asn Tyr Asp Asn Val Arg
    50                  55                  60

Val Glu Phe Lys Asn Lys Asp Leu Ala Asp Lys Tyr Lys Asp Lys Tyr
65                  70                  75                  80

Val Asp Val Phe Gly Ala Asn Tyr Tyr Tyr Gln Cys Tyr Phe Ser Lys
                85                  90                  95

Lys Thr Asn Asp Ile Asn Ser His Gln Thr Asp Lys Arg Lys Thr Cys
                100                 105                 110

Met Tyr Gly Gly Val Thr Glu His Asn Gly Asn Gln Leu Asp Lys Tyr
                115                 120                 125

Arg Ser Ile Thr Val Arg Val Phe Glu Asp Gly Lys Asn Leu Leu Ser
    130                 135                 140

Phe Asp Val Gln Thr Asn Lys Lys Lys Val Thr Ala Gln Glu Leu Asp
145                 150                 155                 160

Tyr Leu Thr Arg His Tyr Leu Val Lys Asn Lys Lys Leu Tyr Glu Phe
                165                 170                 175

Asn Asn Ser Pro Tyr Glu Thr Gly Tyr Ile Lys Phe Ile Glu Asn Glu
                180                 185                 190

Asn Ser Phe Trp Tyr Asp Met Met Pro Ala Pro Gly Asp Lys Phe Asp
    195                 200                 205

Gln Ser Lys Tyr Leu Met Met Tyr Asn Asp Asn Lys Met Val Asp Ser
                210                 215                 220

Lys Asp Val Lys Ile Glu Val Tyr Leu Thr Thr Lys Lys
225                 230                 235
```

<210> SEQ ID NO 4
<211> LENGTH: 203
<212> TYPE: PRT
<213> ORGANISM: Staphylococcus aureus

<400> SEQUENCE: 4

```
Met Phe Lys Lys Tyr Asp Ser Lys Ser Asn Ser Ile Val Leu Lys Ser Ile
1               5                   10                  15
```

```
Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65              70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145             150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
            195                 200

<210> SEQ ID NO 5
<211> LENGTH: 293
<212> TYPE: PRT
<213> ORGANISM: Staphylococcus aureus
<220> FEATURE:
<221> NAME/KEY: MISC_FEATURE
<222> LOCATION: (35)..(35)
<223> OTHER INFORMATION: His can be mutated to Leu

<400> SEQUENCE: 5

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145             150                 155                 160

Thr Asp Lys Lys Val Gly Trp Lys Val Ile Phe Asn Asn Met Val Asn
```

```
                            165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 6
<211> LENGTH: 296
<212> TYPE: PRT
<213> ORGANISM: Staphylococcus aureus
<220> FEATURE:
<221> NAME/KEY: MISC_FEATURE
<222> LOCATION: (149)..(149)
<223> OTHER INFORMATION: His can be mutated to Asp
<220> FEATURE:
<221> NAME/KEY: MISC_FEATURE
<222> LOCATION: (288)..(288)
<223> OTHER INFORMATION: His can be mutated to Asp

<400> SEQUENCE: 6

Glu Ser Lys Lys Asp Asp Thr Asp Leu Lys Leu Val Ser His Asn Val
1               5                   10                  15

Tyr Met Leu Ser Thr Val Leu Tyr Pro Asn Trp Gly Gln Tyr Lys Arg
            20                  25                  30

Ala Asp Leu Ile Gly Gln Ser Ser Tyr Ile Lys Asn Asn Asp Val Val
        35                  40                  45

Ile Phe Asn Glu Ala Phe Asp Asn Gly Ala Ser Asp Lys Leu Leu Ser
    50                  55                  60

Asn Val Lys Lys Glu Tyr Pro Tyr Gln Thr Pro Val Leu Gly Arg Ser
65                  70                  75                  80

Gln Ser Gly Trp Asp Lys Thr Glu Gly Ser Tyr Ser Ser Thr Val Ala
                85                  90                  95

Glu Asp Gly Gly Val Ala Ile Val Ser Lys Tyr Pro Ile Lys Glu Lys
            100                 105                 110

Ile Gln His Val Phe Lys Ser Gly Cys Gly Phe Asp Asn Asp Ser Asn
        115                 120                 125

Lys Gly Phe Val Tyr Thr Lys Ile Glu Lys Asn Gly Lys Asn Val His
    130                 135                 140

Val Ile Gly Thr His Thr Gln Ser Glu Asp Ser Arg Cys Gly Ala Gly
145                 150                 155                 160

His Asp Arg Lys Ile Arg Ala Glu Gln Met Lys Glu Ile Ser Asp Phe
                165                 170                 175
```

Val Lys Lys Lys Asn Ile Pro Lys Asp Glu Thr Val Tyr Ile Gly Gly
            180                 185                 190

Asp Leu Asn Val Asn Lys Gly Thr Pro Glu Phe Lys Asp Met Leu Lys
            195                 200                 205

Asn Leu Asn Val Asn Asp Val Leu Tyr Ala Gly His Asn Ser Thr Trp
            210                 215                 220

Asp Pro Gln Ser Asn Ser Ile Ala Lys Tyr Asn Tyr Pro Asn Gly Lys
225                 230                 235                 240

Pro Glu His Leu Asp Tyr Ile Phe Thr Asp Lys Asp His Lys Gln Pro
                245                 250                 255

Lys Gln Leu Val Asn Glu Val Val Thr Glu Lys Pro Lys Pro Trp Asp
            260                 265                 270

Val Tyr Ala Phe Pro Tyr Tyr Val Tyr Asn Asp Phe Ser Asp His
            275                 280                 285

Tyr Pro Ile Lys Ala Tyr Ser Lys
            290                 295

<210> SEQ ID NO 7
<211> LENGTH: 288
<212> TYPE: PRT
<213> ORGANISM: Staphylococcus aureus

<400> SEQUENCE: 7

Gly Pro Leu Gly Ser Pro Glu Phe Glu Asn Lys Ile Glu Asp Ile Gly
1               5                   10                  15

Gln Gly Ala Glu Ile Ile Lys Arg Thr Gln Asp Ile Thr Ser Lys Arg
            20                  25                  30

Leu Ala Ile Cys Gln Asn Ile Gln Phe Asp Phe Val Lys Asp Lys Lys
        35                  40                  45

Tyr Asn Lys Asp Ala Leu Val Val Lys Met Gln Gly Phe Ile Ser Ser
    50                  55                  60

Arg Thr Thr Tyr Ser Asp Leu Lys Lys Tyr Pro Tyr Ile Lys Arg Met
65                  70                  75                  80

Ile Trp Pro Phe Gln Tyr Asn Ile Ser Leu Lys Thr Lys Asp Ser Asn
                85                  90                  95

Val Asp Leu Ile Asn Tyr Leu Pro Lys Asn Lys Ile Asp Ser Ala Asp
            100                 105                 110

Val Ser Gln Lys Leu Gly Tyr Asn Ile Gly Gly Asn Phe Gln Ser Ala
        115                 120                 125

Pro Ser Ile Gly Gly Ser Gly Ser Phe Asn Tyr Ser Lys Thr Ile Ser
    130                 135                 140

Tyr Asn Gln Lys Asn Tyr Val Thr Glu Val Glu Ser Gln Asn Ser Lys
145                 150                 155                 160

Gly Val Lys Trp Gly Val Lys Ala Asn Ser Phe Val Thr Pro Asn Gly
                165                 170                 175

Gln Val Ser Ala Tyr Asp Gln Tyr Leu Phe Ala Gln Asp Pro Thr Gly
            180                 185                 190

Pro Ala Ala Arg Asp Tyr Phe Val Pro Asp Asn Gln Leu Pro Pro Leu
        195                 200                 205

Ile Gln Ser Gly Phe Asn Pro Ser Phe Ile Thr Thr Leu Ser His Glu
    210                 215                 220

Lys Gly Lys Gly Asp Lys Ser Glu Phe Glu Ile Thr Tyr Gly Arg Asn
225                 230                 235                 240

Met Asp Ala Thr Tyr Ala Tyr Val Thr Arg His Arg Leu Ala Val Asp

```
            245                 250                 255
Arg Lys His Asp Ala Phe Lys Asn Arg Asn Val Thr Val Lys Tyr Glu
            260                 265                 270
Val Asn Trp Lys Thr His Glu Val Lys Ile Lys Ser Ile Thr Pro Lys
            275                 280                 285
```

<210> SEQ ID NO 8
<211> LENGTH: 307
<212> TYPE: PRT
<213> ORGANISM: Staphylococcus aureus

<400> SEQUENCE: 8

```
Gly Pro Leu Gly Ser Pro Glu Phe Glu Gly Lys Ile Thr Pro Val Ser
1               5                   10                  15
Val Lys Lys Val Asp Asp Lys Val Thr Leu Tyr Lys Thr Thr Ala Thr
                20                  25                  30
Ala Asp Ser Asp Lys Phe Lys Ile Ser Gln Ile Leu Thr Phe Asn Phe
            35                  40                  45
Ile Lys Asp Lys Ser Tyr Asp Lys Asp Thr Leu Val Leu Lys Ala Ala
        50                  55                  60
Gly Asn Ile Asn Ser Gly Tyr Glu Lys Pro Asn Pro Asn Asp Tyr Asp
65                  70                  75                  80
Phe Ser Lys Leu Tyr Trp Gly Ala Lys Tyr Asn Val Ser Ile Ser Ser
                85                  90                  95
Gln Ser Asn Asp Ser Val Asn Val Val Asp Tyr Ala Pro Lys Asn Gln
            100                 105                 110
Asn Glu Glu Phe Gln Val Gln Asn Thr Leu Gly Tyr Thr Phe Gly Gly
        115                 120                 125
Asp Ile Ser Ile Ser Asn Gly Leu Ser Gly Gly Leu Asn Gly Asn Thr
130                 135                 140
Ala Phe Ser Glu Thr Ile Asn Tyr Lys Gln Glu Ser Tyr Arg Thr Thr
145                 150                 155                 160
Leu Ser Arg Cys Thr Asn Tyr Lys Asn Val Gly Trp Gly Val Glu Ala
                165                 170                 175
His Lys Ile Met Asn Asn Gly Trp Gly Pro Tyr Gly Arg Asp Ser Phe
            180                 185                 190
His Pro Thr Tyr Gly Asn Glu Leu Phe Leu Ala Gly Arg Gln Ser Ser
        195                 200                 205
Ala Tyr Ala Gly Gln Asn Phe Ile Ala Gln His Gln Met Pro Leu Leu
210                 215                 220
Ser Arg Ser Asn Phe Asn Pro Glu Phe Leu Ser Val Leu Ser His Arg
225                 230                 235                 240
Gln Asp Gly Ala Lys Lys Ser Lys Ile Thr Val Thr Tyr Gln Arg Glu
                245                 250                 255
Met Asp Leu Tyr Gln Ile Arg Trp Asn Gly Phe Tyr Trp Ala Gly Ala
            260                 265                 270
Asn Tyr Lys Asn Phe Lys Thr Arg Thr Phe Lys Ser Thr Tyr Glu Ile
        275                 280                 285
Asp Trp Glu Asn His Lys Val Lys Leu Leu Asp Thr Lys Glu Thr Glu
290                 295                 300
Asn Asn Lys
305
```

COMPOSITIONS AND METHODS FOR INDUCING IMMUNE RESPONSES AGAINST BACTERIA IN THE GENUS *STAPHYLOCOCCUS*

CROSS-REFERENCE TO RELATED APPLICATIONS

This application is a National Stage Application under 35 U.S.C. §371 and claims the benefit of International Application No. PCT/US2012/029434, filed Mar. 16, 2012, which claims priority to U.S. Provisional Application No. 61/453,216, filed Mar. 16, 2011. The disclosures of the prior applications are considered part of (and are incorporated by reference in) the disclosure of this application.

The instant application includes a sequence listing in electronic medium and submitted to the United States Patent and Trademark Office via the electronic filing system. The ASCII text file, which is incorporated-by-reference herein, is titled "Substitute-09531-0317US1_ST25.txt," was created on Nov. 2, 2015, and has a size of 20 kilobytes.

STATEMENT REGARDING FEDERALLY SPONSORED RESEARCH OR DEVELOPMENT

This invention was made with government support under R01-AI074283 and U54-AI057153 awarded by the National Institutes of Health. The government has certain rights in the invention.

TECHNICAL FIELD

This document relates to compositions containing staphylococcal toxoids, and more particularly to compositions comprising two or more staphylococcal toxoids and methods for inducing an immune response to two or more staphylococcal exotoxins produced by a strain of *Staphylococcus* in a subject.

BACKGROUND

*Staphylococcus aureus* is considered the most significant cause of serious infectious diseases in the United States; this is likely to be true world-wide as well. See, Klevens et al., *JAMA* 298:1763-1771 (2007); and Lowy, *N Engl J Med* 339:520-532 (1998). Serious illnesses caused by the organism include highly fatal pneumonia, in which as many as 35,000 patients succumb each year, infectious endocarditis, where *S. aureus* is the cause of up to 20,000 cases (10,000 fatalities, and significant survivor strokes and metastatic abscesses due to microbial clumps seeding the brain and other organs), sepsis where the organism is the second leading cause of bloodstream infections (for example 800,000 post-surgical infections), and osteomyelitis (*S. aureus* is the cause of nearly all cases). Additionally, *S. aureus* has become highly antibiotic resistant, with both community-associated and hospital-associated methicillin-resistant *S. aureus* (MRSA) arising.

There have been major efforts by the medical and scientific communities to develop vaccines against *S. aureus*. However, all of them resulted in failure to date. Thus, there is a need for a vaccine against *S. aureus*.

SUMMARY

As described herein, administration of compositions containing two or more staphylococcal toxoids to animal models of human staphylococcal pneumonia and infection endocarditis completely protected the animals from challenge with *S. aureus*. Compositions described herein can be used for active immunization against bacteria of the genus *Staphylococcus*. In addition, compositions described herein can be used for generating antibodies for use as, for example, passive immunotherapeutic agents. Without being bound to a particular mechanism, *Staphylococcus* produces exotoxins to facilitate the organism's ability to cause infection. Thus, the compositions described herein can be used to enhance a subject's immune response to two or more staphylococcal exotoxins such that activity of the exotoxins is neutralized in the subject. Specifically, the staphylococcal exotoxins, which are in the family of molecules known as superantigens, contain a human cell receptor interaction site on CD40.

As described herein, non-toxic superantigen mutants can amplify immune responses to a second antigen, staphylococcal β-toxin, by 10 to 100-fold, as well as other antigens such as HIV proteins or sheep erythrocytes. In addition, antibodies against TSST-1 toxoids are capable of neutralizing superantigenicity and capable of protecting rabbits from lethal challenge by native TSST-1. Patients with staphylococcal TSS do not develop neutralizing antibody responses to the superantigen TSST-1, and thus they remain susceptible to TSS recurrences. This effect results from immune dysfunction due to TSST-1, rather than genetic inability to recognize the superantigen as foreign. TSST-1 toxoids described herein stimulate protective immunity against native TSST-1 and function as adjuvants to amplify antibody responses to secondary antigens. This effect is not seen with use of wild-type TSST-1, which is more likely to result in antibody immunosuppression than in adjuvanticity.

In one aspect, this document features compositions that include two or more staphylococcal toxoids, wherein the toxoids are selected from the group consisting of a toxic shock syndrome toxin-1 (TSST-1) toxoid, a staphylococcal enterotoxin B (SEB) toxoid, a staphylococcal enterotoxin C (SEC) toxoid, a staphylococcal enterotoxin-like X (SEL-X) toxoid, an alpha toxin toxoid, a beta toxin toxoid, and a gamma toxin toxoid. The TSST-1 toxoid can include a serine residue at position 31 and a proline residue at position 32. The TSST-1 toxoid can be a fusion protein (e.g., a fusion of residues 1 to 89 of human TSST-1 and residues 90 to 195 of ovine TSST-1). The TSST-1 toxoid can include an alanine at position 135. The TSST-1 toxoid can include an alanine at position 136. The SEB toxoid can include one or more of the following: an alanine residue at position 90, a valine residue at position 91, and an alanine residue at position 210. The SEC toxoid can be a SEC3 toxoid. The SEC toxoid can include an alanine residue at position 90 and/or an alanine residue at position 210. The alpha toxin toxoid can include a leucine residue at position 35. The beta toxin toxoid can include an asparagine at position 149 and/or an asparagine at position 288. In some embodiments, the composition includes three staphylococcal toxoids. In some embodiments, the composition includes four staphylococcal toxoids. In some embodiments, the composition includes five staphylococcal toxoids. In some embodiments, the composition includes a TSST-1 toxoid, an SEB toxoid, an SEC toxoid, an alpha toxoid, and a beta toxoid. Such a composition further can include an SEL-X toxoid and/or a gamma toxin toxoid. In any of the compositions described herein, the gamma toxin toxoid can be a single chain of the gamma *Staphylococcus* toxin (e.g., the B chain of the gamma

*Staphylococcus* toxin). In some embodiments, the composition includes a SEC toxoid, a SEB toxoid, and an alpha toxoid.

Any of the compositions described herein further can include an adjuvant (e.g., incomplete Freund's adjuvant, complete Freund's adjuvant, or an aluminum salt).

This document also features a method for inducing an immune response to two or more staphylococcal exotoxins produced by a strain of *Staphylococcus* in a subject. The method includes administering to the subject an amount of a pharmaceutical composition effective to induce the immune response, the pharmaceutical composition including two or more staphylococcal toxoids, wherein the toxoids are selected from the group consisting of a TSST-1 toxoid, an SEB toxoid, an SEC toxoid, an SEL-X toxoid, an alpha toxin toxoid, and a beta toxin toxoid. The composition can be administered subcutaneously or intramuscularly. The method further can include determining if the blood of the subject contains antibodies having specific binding affinity for one or more of the staphylococcal toxoids. The method further comprising determining if the blood of the subject contains antibodies having specific binding affinity for one or more of the staphylococcal exotoxins. The strain of *Staphylococcus* can be methicillin-resistant or methicillin-sensitive. The strain can be an isolate of USA400, USA300, or USA200. Any of the compositions described herein can be used in the methods.

In another aspect, this document features a composition that includes a TSST-1 toxoid, an SEB toxoid, an SEC toxoid, a staphylococcal alpha toxin toxoid, a staphylococcal beta toxin toxoid, and a single chain of the gamma staphylococcal toxin. The composition further can include an adjuvant (e.g., incomplete Freund's adjuvant, complete Freund's adjuvant, or an aluminum salt).

In another aspect, this document features a composition that includes a TSST-1 toxoid, an SEC toxoid, a staphylococcal alpha toxin toxoid, a staphylococcal beta toxin toxoid, and a single chain of the gamma staphylococcal toxin. The composition further can include an adjuvant (e.g., incomplete Freund's adjuvant, complete Freund's adjuvant, or an aluminum salt). Such a composition further can include a SEB toxoid.

In another aspect, this document features a composition that includes a TSST-1 toxoid, an SEC toxoid, and a staphylococcal alpha toxin toxoid. Such a composition further can include a SEB toxoid. The composition further can include an adjuvant (e.g., incomplete Freund's adjuvant, complete Freund's adjuvant, or an aluminum salt).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DESCRIPTION OF DRAWINGS

FIG. 1 is a bar graph depicting the four hour change in temperature in rabbits after challenge with toxoid mutants of toxic shock syndrome toxin-1 (TSST-1) (G31S/S32P and Huvine, 1000 µg/kg) (10 rabbits per toxoid challenge) or wild-type TSST-1 (1 µg/kg) (5 rabbits). At the 4 hour time point, all rabbits were challenged with 50 µg/kg of lipopolysaccharide (LPS) (1/10 $LD_{50}$) alone. There is a $10^6$-fold synergy between superantigens (TSST-1) and LPS in causing lethal TSS.

FIG. 2 is bar graph depicting the four hour change in temperature in rabbits after challenge with toxoid mutant SEC Y90A (10 rabbits, 1000 µg/kg) or wild-type SEC3 (5 rabbits, 1 µg/kg). At the 4 hour time point, all rabbits were challenged with 50 µg/kg of LPS (1/10 $LD_{50}$) alone. There is a $10^6$-fold synergy between superantigens (SEC3) and LPS in causing lethal TSS.

FIG. 6 is a bar graph indicating the number of alive rabbits (prior immunization with a toxoid or non-immunized) after challenge with wild-type TSST-1. Prior immunization with G31S/S32P or Huvine toxoids protected rabbits from TSST-1 lethality. Animals were monitored 15 days for health.

FIG. 13 is a bar graph depicting the temperature (° C.) and survival of rabbits immunized or not immunized against alpha toxin and the respective superantigen (SEC or SEC) produced by the challenge CA-MRSA strain when organisms were administered intra-pulmonary. Fevers were measured with the use of rectal thermometers prior to infection and on day 1 post-infection. Deaths were recorded over a 7 day time-period.

DETAILED DESCRIPTION

Figure 3:
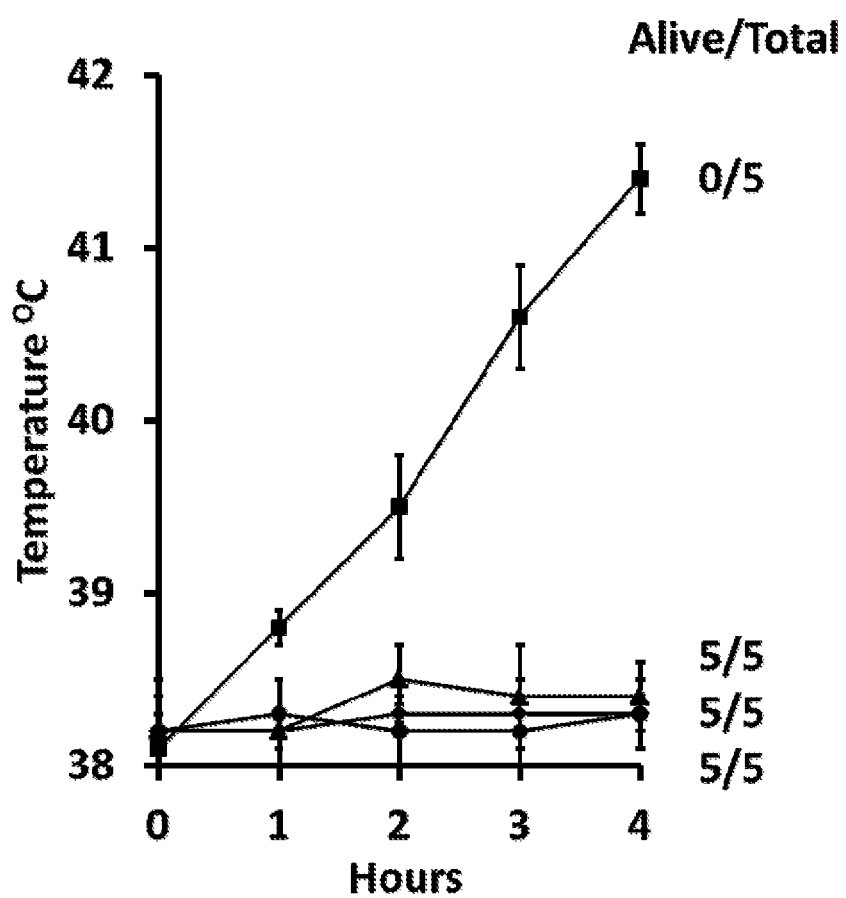
FIG. 3 is a graph depicting the temperature (° C.) in rabbits after challenge with toxoid mutants of toxic shock syndrome toxin-1 (TSST-1) ((■), G31S/S32P; (♦), H135A (▲); and Q136A (●)) (5 rabbits per toxoid challenge) or wild-type TSST-1 (1 µg/kg) (5 rabbits). At the 4 hour time point, just after taking the 4 hr temperatures, all rabbits were challenged with 100 µg/kg of LPS alone. Alive/Total refers to the number of animals that survived as measured 48 hr post LPS injection.

In general, the document provides compositions containing two or more staphylococcal toxoids (e.g., two, three, four, five, six, or seven staphylococcal toxoids). As used herein, toxoid refers to a toxin with at least a 10$^6$-fold reduction in biological activity as compared to the corresponding wild-type toxin and which retains immunogenicity. Some staphylococcal toxoids include one or more mutations that reduce biological activity. In some embodiments, a staphylococcal toxoid can refer to a single protein component of a toxin that requires two different protein components to produce a biologically active toxin. In some embodiments, a non-toxic amount of a toxin is used instead of, or in addition to, a staphylococcal toxoid.

As described herein, the toxoids, specifically the superantigen toxoids, amplify immune responses to each other and other proteins through a site on some or all of them that interacts with CD40 on B cells. See, Example 9. This finding indicates that humans may not have to receive booster vaccinations every 8-10 years as is the case with some other toxoid vaccines (e.g., tetanus). In addition, immunizing doses may be smaller, resulting in less vaccine injection site discomfort. Furthermore, these superantigen toxoids may be added to other established vaccines (e.g., tetanus, diphtheria, pneumonococcal, *Haemophilus*, pertussis, or *Neisseria*) to amplify immune responses in the same way. In some embodiments, suitable staphylococcal toxoids bind to CD40 but lack detectable binding to MHC II molecules or the β-chain of the T cell receptor (Vβ-TCR).

A composition described herein can include two or more (e.g., three or more, four or more, five or more, six or more, or seven or more) of a toxic shock syndrome toxin-1 (TSST-1) toxoid, a staphylococcal enterotoxin B (SEB) toxoid, a staphylococcal enterotoxin C (SEC) toxoid, a staphylococcal enterotoxin-like X (SEL-X) toxoid, an alpha toxin toxoid, a beta toxin toxoid, or a gamma toxin toxoid.

TSST-1 toxoids can include one or more mutations (e.g., at positions 31, 32, 135, 136, or 139). For example, a TSST-1 toxoid can include mutations at positions 31 and 32 of SEQ ID NO:1. STNDNIKDLLDWYSSGSDTFTNSEV-LDNSLGSMRIKNTDGSISLIIFPSPYYSPAFTKGEK VDLNTKRTKKSQHTSEGTYIHFQISGVTNTEKLPT-PIELPLKVKVHGKDSPLKYWPKFDK KQLAISTLD-FEIRHQLTQIHGLYRSSDKTGGYWKITMNDGSTYQS-DLSKKFEYNTEKPPI NIDEIKTIEAEIN.

For example, a TSST-1 toxoid can include a serine substituted for glycine at position 31 of SEQ ID NO:1 and a proline substituted for serine at position 32 of SEQ ID NO:1 (G31S/S32P). A TSST-1 toxoid also can include an alanine substituted for a histidine at position 135 of SEQ ID NO:1 (H135A), alanine substituted for a glutamine at position 136 of SEQ ID NO:1 (Q136A), or alanine substituted for glutamine at position 139 of SEQ ID NO:1 (Q139A). TSST-1 G31S/S32P lacks ability to bind to MHC II molecules, and TSST-1 H135A, Q136A, and Q139A lack ability to bind to Vβ-TCR.

A TSST-1 toxoid also can be a fusion protein of the human isolate of TSST-1 toxin and an ovine isolate TSST-1 toxin, which contains amino acid differences at positions 19, 55, 57, 69, 80, 132, and 140 of SEQ ID NO:1 relative to the mature human TSST-1 isolate. To produce the fusion protein, portions of the tstH (human isolate) and tstO (ovine isolate) genes were ligated to yield a human-ovine gene fusion, referred to as huvine protein. The huvine protein contains the first 89 amino acids from TSST-1 (human isolate) and the last 105 amino acids from a TSST-Ovine isolate. Huvine is not T cell mitogenic, and does not elicit toxic shock syndrome in rabbit models. See, for example Murray et al., *J. Immunol.* 152(1):87-95 (1994).

As described in Examples 2 and 4, TSST-1 toxoids G31S/S32P, huvine, H135A, and Q136A are biologically inactive and inactivated by at least 10$^6$-fold compared to wild-type TSST-1.

SEB and SEC toxoids can include one or more mutations (e.g., at positions 20, 23, 90, 91, or 210). See, for example, Leder et al., *J Exp Med.* 187(6): 823-833 (1998). For example, an SEC toxoid can be an SEC3 toxoid having a mutation at position 90 of SEQ ID NO:2: ESQPDPMPD-DLHKSSEFTGTMGNMKYLYDDHYVSATKVKSVDK-FLAHDLIYNIS DKKLKNYDKVKTELLNEDLAK-KYKDEVVDVYGSNYYVNCYFSSKDNVGKVTG GKTCMYGGITKHEGNHFDNGNLQNVLVRVYENK-RNTISFEVQTDKKSVTAQEL DIKARNFLINKKNLYEF-NSSPYETGYIKFIENNGNTFWYDMMPAPGD-KFDQSKYL MMYNDNKTVDSKSVKIEVHLTTKNG. For example, an SEC3 toxoid can include an alanine substituted for asparagines at position 23 of SEQ ID NO:2. For example, an SEC3 toxoid can include an alanine substituted for tyrosine at position 90 of SEQ ID NO:2. An SEC3 toxoid can include an alanine substituted for glutamine at position 210 of SEQ ID NO:2.

An SEB toxoid can have a mutation at position 20, 26, 90, 91, or 210 of SEQ ID NO:3: ESQPDPKPDELHKSSKF-TGLMENMKVLYDDNHVSAINVKSIDQFLYFDL1YSI-KD TKLGNYDNVRVEFKNKDLADKYKDKYVDVFG-ANYYYQCYFSKKTNDINSHQT DKRKTCMYGGVT-EHNGNQLDKYRSITVRVFEDGKNLLSFDVQTNKKK-VTAQEL DYLTRHYLVKNKKLYEFNNSPYETGYIK-FIENENSFWYDMMPAPGDKFDQSKYL MMYNDNK-MVDSKDVKIEVYLTTKKK. For example, an SEB toxoid can include an alanine substituted for tyrosine at position 90 of SEQ ID NO:3. An SEB toxoid can include an alanine substituted for glutamine at position 210 of SEQ ID NO:3. An SEB toxoid can include a valine substituted for tyrosine at position 91 of SEQ ID NO:3. In another embodiment, an SEB toxoid can include a threonine substituted for leucine at position 20, a tyrosine substituted for valine, and a valine substituted for tyrosine at position 91 of SEQ ID NO:3. As described in Examples 2 and 4, SEC3 Y90A is inactivated by at least $10^6$-fold compared to wild-type SEC3.

SE1-X toxoids can include one or more mutations (e.g., at residues corresponding to positions 31, 32, 135, 136, 139, or 140 of SEQ ID NO:1). For example, a SE1-X toxoid can include mutations in SEQ ID NO:4 (MFKKYDSKNSIV-LKSILSLGIIYGGTFGIYPKADASTQNSSSVQD-KQLQKVEEVP NNSEKALVKKLYDRYSKDTINGK-SNKSRNWVYSERPLNENQVRIHLEGTYTVAG RVYTPKRNITLNKEVVTLKELDHIIRFAHISYG-LYMGEHLPKGNIVINTKDGGKYT LESHKELQK-DRENVKINTADIKNVTFKLVKSVNDIEQV) that correspond to positions 31 and 32 of SEQ ID NO:1.

An alpha-toxin toxoid can have one or more mutations (e.g., at position 35). For example, an alpha-toxin toxoid can include a mutation at position 35 of SEQ ID NO:5: ADS-DINIKTGTTDIGSNTTVKTGDLVTYDKENGMHKKV-FYSFIDDKNHNKKLLVI RTKGTIAGQYRVYSEEGA-NKSGLAWPSAFKVQLQLPDNEVAQISDYYPRNSIDT KEYMSTLTYGFNGNVTGDDTGKIGGLIGANVSIGHT-LKYVQPDFKTILESPTDKK VGWKVIFNNMVNQN-WGPYDRDSWNPVYGNQLFMKTRNGSMKAADN-FLDPNK ASSLLSSGFSPDFATVITMDRKASKQQTN-IDVIYERVRDDYQLHWTSTNWKGTN TKDKWT-DRSSERYKIDWEKEEMTN.

For example, a leucine can be substituted for histidine at position 35 of SEQ ID NO:5. See, for example, WO 2009/029831. As described below in Examples 6 and 7, rabbits immunized against G31S/S32P alone or in combination with alpha toxin were completely protected from challenge with a strain of *S. aureus*. However, immunization with alpha toxin alone only partially protected the animals.

A beta-toxin toxoid can have one or more mutations (e.g., at positions 149 or 288). For example, a beta-toxin toxoid can include a mutation at positions 149 and 288 of SEQ ID NO:6: ESKKDDTDLKLVSHNVYMLSTVLYPN-WGQYKRADLIGQSSYIKNNDVVIFNEAF DNGASD-KLLSNVKKEYPYQTPVLGRSQSGWDKTEGSYSST-VAEDGGVAIVSKYP IKEKIQHVFKSGCGFDNDSNK-GFVYTKIEKNGKNVHVIGTHTQSEDSRCGAGHD RKIRAEQMKEISDFVKKKNIPKDETVYIGGDLNVNK-GTPEFKDMLKNLNVNDVL YAGHNSTWDPQSNSI-AKYNYPNGKPEHLDYIFTDKDHKQPKQLVNEV-VTEKPKP WDVYAFPYYYVYNDFSDHYPIKAYSK. For example, an asparagine can be substituted for histidine at position 149 and an asparagine substituted for histidine at position 288 of SEQ ID NO:6. See, for example, Huseby et al., *J. Bacteriol.*, 189(23): 8719-8726 (2007).

Gamma toxin depends on two different protein components, and each component alone is immunogenic but not toxic. The A protein of gamma toxins pairs up with either B or C to create active protein. Thus, a composition can include an A, B, or C protein of gamma toxin. The B protein is particularly useful in compositions described herein as it has no toxicity alone. SEQ ID NO:7 is the amino acid sequence of the A chain: GPLGSPEFENKIEDIGQ-GAEIIKRTQDITSKRLAICQNIQFDFVKDK-KYNKDALVV KMQGFISSRTTYSDLKKYPYIKRMI-WPFQYNISLKTKDSNVDLINYLPKNKIDSAD VSQKLGYNIGGNFQSAPSIGGSGSFNYSKTISYN-QKNYVTEVESQNSKGVKWGV KANSFVTPNGQVS-AYDQYLFAQDPTGPAARDYFVPDNQLPPLIQSGF-NPSFITTLS HEKGKGDKSEFEITYGRNMDATYAY-VTRHRLAVDRKHDAFKNRNVTVKYEVN WKTHEVKIKSITPK. SEQ ID NO:8 is the amino acid sequence of the B chain: GPLGSPEFEGKITPVSVKKVD-DKVTLYKTTATADSDKFKISQILTFNFIKDKSYDK DTLVLKAAGNINSGYEKPNPNDYDFSKLYWGAKYN-VSISSQSNDSVNVVDYAP KNQNEEFQVQNTLGYTF-GGDISISNGLSGGLNGNTAFSETINYKQESYRTTLS-RCT NYKNVGWGVEAHKIMNNGWGPYGRDSFHP-TYGNELFLAGRQSSAYAGQNFIA QHQMPLLSRSNFN-PEFLSVLSHRQDGAKKSKITVTYQREMDLYQIR-WNGFYWA GANYKNFKTRTFKSTYEIDWENHKV-KLLDTKETENNK.

In some experiments, a composition described herein can include a TSST-1 toxoid (e.g., G31S/S32P, H135A, Q136A, and/or Huvine), an SEC toxoid (e.g., SECY90A and/or Q210A), and an alpha toxin toxoid (e.g., H35L). Such a composition further can include one or more of the following: an SEB toxoid (e.g., SECY90A and/or Q210A), a beta-toxin toxoid (e.g., H149N, H288N), a gamma-toxin toxoid (e.g., B chain of gamma toxin) and an SE1-X toxoid.

In some embodiments, a composition described herein can include a TSST-1 toxoid (e.g., G31S/S32P, H135A, Q136A, and/or Huvine), an SEC toxoid (e.g., SECY90A and/or Q210A), an SEB toxoid (e.g., SECY90A and/or Q210A), an alpha toxin toxoid (e.g., H35L), and a beta-toxin toxoid (e.g., H149N, H288N). Such a composition further can include a gamma-toxin toxoid (e.g., B chain of gamma toxin) and/or an SE1-X toxoid.

Toxins and toxoids described herein can be manufactured by standard in vitro recombinant DNA techniques and in vivo transgenesis using nucleotide sequences encoding the appropriate polypeptides. Methods well-known to those skilled in the art can be used introduce mutations and construct expression vectors containing relevant coding sequences and appropriate transcriptional/translational regulatory elements. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology [Green Publishing Associates and Wiley Interscience, N.Y., 1989].

The transcriptional/translational regulatory elements referred to above include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors.

The expression systems that may be used for purposes of the invention include but are not limited to microorganisms such as bacteria (for example, *E. coli* and *B. subtilis*) transformed with recombinant bacteriophage DNA, plasmid DNA, or cosmid DNA expression vectors containing nucleic acid molecules encoding enhancing agents or immunogenic stimuli; yeast (for example, *Saccharomyces* and *Pichia*) transformed with recombinant yeast expression vectors containing a nucleic acid encoding enhancing agents or immunogenic stimuli; insect cell systems infected with recombinant virus expression vectors (for example, baculovirus) containing a nucleic acid encoding enhancing agents or immunogenic stimuli; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing a nucleotide sequence encoding; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

Cells transfected or transduced with the expression vectors described herein can then be used, for example, for large or small scale in vitro manufacture of toxoids by methods known in the art. In essence, such methods involve culturing the cells under conditions that maximize production of the polypeptide and isolating the polypeptide from the culture, i.e., the cells and/or the culture medium. Methods for purifying biological macromolecules (e.g., proteins) are known in the art. For example, toxoids described herein can be purified by combinations of ethanol precipitation and isoelectric focusing from culture fluids of clones containing the mutated genes. See, Blomster-Hautamaa and Schlievert, *Methods Enzymol* 165:37-43 (11) (1988). The degree of purity of the macromolecules can be measured by any appropriate method, e.g., column chromatography, polyacrylamide gel electrophoresis, or HPLC analysis.

Compositions containing two or more staphylococcal toxoids can be used as prophylactic vaccines against diseases caused by bacteria of the genus *Staphylococcus*. Compositions described herein also can be used for generating antibodies against two or more staphylococcal exotoxins for use as, for example, passive immunotherapeutic agents. For example, compositions described herein can be used as vaccines against diseases caused by *S. aureus* (including methicillin resistant strains of *S. aureus* such as USA400, USA300, or USA200), *S. intermedius*, *S. epidermidis*, *S. lugdunensis*, *S. schleiferi*, *S. caprae*, *S. saprophyticus*, *S. leei*, other coagulase negative or positive Staphylococci. USA300 and USA400 are community-associated methicillin-resistant *Staphylococcus aureus* (CA-MRSA) strains. USA400 strains, including strains MW2 and c99-529, which were isolated from the original association of USA400 with necrotizing pneumonia, are a potent cause of necrotizing pneumonia. See, *JAMA* 282:1123-5 (1999); and Fey, et al. *Antimicrob Agents Chemother* 47:196-203 (2003).

Diseases caused by *S. aureus*, include, for example, toxic shock syndrome, pneumonia, infectious endocarditis, sepsis, skin infections, soft tissue abscesses, gastroenteritis, and osteomyelitis. The term "prophylaxis," as used herein, refers to the complete prevention of the symptoms of a disease, a delay in onset of the symptoms of a disease, or a lessening in the severity of subsequently developed disease symptoms. For example, for *S. aureus*, a prophylactic vaccine can prevent development of pneumonia, sepsis, infectious endocarditis, or osteomyelitis, delay the onset of symptoms of pneumonia, sepsis, infectious endocarditis, or osteomyelitis, or lessen the severity of subsequently developed symptoms of pneumonia, sepsis, infectious endocarditis, or osteomyelitis. The compositions described herein can be used to induce an immune response to a staphylococcal exotoxin in humans and other animals, including rabbits, mice, ferrets, dogs, and chickens.

As used herein, "immune response" refers to the development of a humoral (antibody mediated), cellular (mediated by antigen-specific T cells or their secretion products) or both humoral and cellular response directed against a staphylococcal exotoxin in a recipient patient. Such a response can be an active response induced by administration of immunogen or a passive response induced by administration of antibody, antibody containing material, or primed T-cells. As used herein "active immunity" refers to any immunity conferred upon a subject by administration of an antigen. As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition can be used in passive immunization for the prevention or treatment of infection by Staphylococcal organisms. The antibody component can be a polyclonal antiserum. In certain aspects the antibody or antibodies are affinity purified from an animal or second subject that has been challenged with the compositions described herein.

In some embodiments, a composition containing a plurality of *Staphylococcus* toxoids is administered to a subject. Toxoids described herein possess inherent adjuvant activity in that they significantly synergize with other antigens to amplify antibody responses. As such, compositions described herein do not require a separate adjuvant to be included.

In some embodiments, a composition containing a plurality of *Staphylococcus* toxoids and an adjuvant is administered to the subject. An "adjuvant" is an immunological compound that can enhance an immune response against a particular antigen such as a polypeptide. Suitable adjuvants can be selected based, for example, on the route of administration and number of administrations. Non-limiting examples of adjuvants include mineral oil adjuvants such as Freund's complete and incomplete adjuvant, and Montanide incomplete seppic adjuvant (ISA, available from Seppic, Inc., Paris, France); oil-in-water emulsion adjuvants such as the Ribi adjuvant system (RAS); TiterMax®, and syntax adjuvant formulation containing muramyl dipeptide; squalene; or aluminum salt adjuvants (e.g., aluminum phosphate, aluminum hydroxide, or Alum).

Compositions described herein can include a pharmaceutically acceptable excipient, such as phosphate buffered saline or bicarbonate (e.g., 0.24 M NaHCO$_3$). Suitable excipients can be chosen by one of ordinary skill in the art on the basis of the mode and route of administration, and standard pharmaceutical practice. Pharmaceutical excipients and diluents, as well as pharmaceutical necessities for their use, are described, e.g., in Remington's Pharmaceutical Sciences. Non-limiting examples of pharmaceutical excipients include solvent (e.g., water or physiological saline), solubilizing agent (e.g., ethanol, polysorbates, or Cremophor EL7), agent for achieving isotonicity, preservative, antioxidizing agent, lactose, starch, crystalline cellulose, mannitol, maltose, calcium hydrogen phosphate, light silicic acid anhydride, calcium carbonate, binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils). If desired, glycerin, dimethylacetamide, 70% sodium lactate, surfactant, or basic substance such as sodium hydroxide, ethylenediamine, ethanolamine, sodium bicarbonate, arginine, meglumine, or trisaminomethane can be added. Biodegradable polymers such as poly-D,L-lactide-co-glycolide or polyglycolide can be used as a bulk matrix if slow release of the composition is desired (see e.g., U.S. Pat. Nos. 5,417,986, 4,675,381, and 4,450,150). Pharmaceutical preparations such as solutions, tablets, granules or capsules can be formed with these components. If the composition is administered orally, flavorings and/or colors can be added.

Generally, the composition to be administered can be suspended in a pharmaceutically-acceptable excipient (e.g., physiological saline) and administered orally, transdermally, intravenously, subcutaneously, intramuscularly, intraocularly, intraperitoneally, intrarectally, intravaginally, intranasally, intragastrically, intratracheally, intrapulmonarily, or any combination thereof. For example, the composition can be administered intranasally and subcutaneously. If desired, booster immunizations may be given once or several times (e.g., 2, 3, or 4 times) at various intervals (e.g., three months apart or three years apart). For example, for a prophylactic vaccine, a priming dose can be followed by one or several booster immunizations (e.g., three booster doses) at various intervals (e.g., spaced one week apart). For example, a booster shot can be given at 8 to 12 weeks after the first immunization, and a second booster can be given at 16 to 20 weeks, using the same formulation.

Suitable doses of the composition elicit an immune response in the subject but do not cause the subject to develop severe clinical signs of staphylococcal infection. The dose required to elicit an immune response depends on the route of administration, the nature of the composition, the subject's size, weight, surface area, age, and sex, other drugs being administered, and the judgment of the attending physician. Wide variations in the needed dose are to be expected in view of differing efficiencies of various routes of administration. For example, oral administration would be expected to require higher doses than administration by intravenous injection. Variations in these dose levels can be adjusted using standard empirical routines for optimization, as is well understood in the art. Encapsulation of the composition in a suitable delivery vehicle (e.g., polymeric microparticles or implantable devices) may increase the efficiency of delivery, particularly for oral delivery.

To determine if an immune response was induced in the subject, a biological sample from the subject can be examined to determine if it contains detectable amounts of antibodies having specific binding affinity for one or more of the toxoids the subject was vaccinated against. The biological sample can be blood (e.g., serum) or a mucosal sample (e.g., saliva). Methods for detecting antibodies, including IgG, IgM, and IgA, are known, and can include, for example, enzyme-linked immunosorbent assays (ELISA) or Western blotting.

Articles of Manufacture

Compositions described herein can be combined with packaging material and sold as articles of manufacture or kits. Components and methods for producing articles of manufactures are well known. The articles of manufacture may combine one or more therapeutic compositions described herein. In addition, the articles of manufacture may further include sterile water, pharmaceutical carriers, buffers, antibodies, indicator molecules, and/or other useful reagents for detecting microbial diseases. Instructions describing how a composition or vaccine is effective for preventing the incidence of an infection, preventing the occurrence of the clinical signs of an infection, ameliorating the clinical signs of an infection, lowering the risk of the clinical signs of an infection, lowering the occurrence of the clinical signs of an infection and/or reducing the spread of infections may be included in such kits. A composition described herein may be provided in a pre-packaged form in quantities sufficient for a single administration.

The following are examples of the practice of the invention. They are not to be construed as limiting the scope of the invention in any way.

EXAMPLES

Example 1

Methods and Materials

*S. aureus* strain RN4220 containing plasmids encoding TSST-1, TSST-1 mutants, or SEC were used as sources of TSST-1, TSST-1 mutants, or SEC. See, Leder et al., *J Exp Med*, 187:823-33 (1998); Murray et al., *Infect Immun,* 64:371-4 (1996); and Murray et al., *J Immunol,* 152:87-95 (1994). Strain RN4220 does not produce detectable endogenous superantigens. RN4220 also was used as the source of β-toxin. See, Gaskin et al., *Protein Expr Purif* 9:76-82S (1997).

*S. aureus* strain MNPE was the source of native α-toxin. See, Lin et al., *Biochemistry* 50:7157-67 (2011). *Escherichia coli* clones were the sources of mutant α-toxin (H35L), as provided by Dr. Juliane Bubeck-Wardenburg, University of Chicago, and γ-toxin as expressed from a pET vector. See, Bubeck-Wardenburg and Schneewind, *J Exp Med* 205:287-94S (2008).

*S. aureus* strain MNPE was used in microbial challenge studies; this organism caused a fatal case of post-influenza TSS in Minnesota. See, MacDonald et al., *JAMA,* 257:1053-8 (1987). MNPE is an isolate of USA200; these organisms cause the majority of TSS cases. See Schlievert et al., *J Allergy Clin Immunol* 125:39-49 (2010). MNPE has the following secreted virulence factor phenotype: TSST-1$^{high+}$, SEC$^{high+}$, α-toxin$^{high+}$, β-toxin$^{high+}$, and γ-toxin$^+$. See, Lin et al., 2011, supra. For use in pneumonia and infective endocarditis/sepsis studies, the organism was grown overnight in 25 ml of Todd-Hewitt (Difco Laboratories, Detroit, Mich.) broth at 37° C. with shaking at 200 revolutions per min under standard air conditions. See, Schlievert et al., *Infect Dis* 147:236-42 (1983). The organism was washed one time with phosphate-buffered saline (PBS; 0.005M sodium phosphate, pH 7.2; 0.15 M NaCl), centrifuged at 14,000×g, for 5 min, and then resuspended in Todd Hewitt medium at 2×10$^9$/0.2 ml volume for high-dose injection in pneumonia studies (Strandberg et al., *J Infect Dis* 202: 1690-7 (2010)), and in PBS at 1×10$^8$/ml, with 2 ml being injected intravenously for infective endocarditis/sepsis studies (Schlievert et al., *Infect Immun*, 66:218-23 (1998)).

Toxoid vaccine candidates of TSST-1 included G31S/S32P (where position 31 is changed from a glycine to a serine, and position 32 is changed from a serine to a proline), H135A (where position 135 is changed from a histidine to an alanine), Q136A (where position 136 is changed from a glutamine to an alanine), and huvine (a gene fusion of human and ovine TSST; these proteins differ by seven amino acids). The G31S/S32P protein is biologically inactive due to mutations in the site on the exotoxin that binds to MHC II molecules, which is required for toxicity. See Kim et al., *Science*, 266:1870-1874 (1994). The huvine protein also is biologically inactive. See Murray et al., *J Immunol* 152:87-95 (1994). The H135A protein fails to bind the variable part of the β chain of the T cell receptor (Vβ-TCR), and the Q136A protein also fails to bind to Vβ-TCR. See, Jardetzky et al., *Nature* 368:711-8 (1994); McCormick et al., *J Immunol* 171:1385-92 (2003); and Murray et al., *Infect Immun* 64:371-4 (1996).

The G31S/S32P, H135A, and Q136A site-specific mutants of TSST-1 were prepared through use of the Quikchange method (Stratagene, La Jolla, Calif.). The initial plasmid was native tstH, on a shuttle plasmid pCE104, cloned into *E. coli*. See, Murray et al., 1996, supra. After performing mutagenesis, the resultant plasmids were cloned into *E. coli* and the sequences of the entire structural genes were verified to confirm the TSST-1 mutations. The plasmids were then cloned into *S. aureus* RN4220 for production and purification. The huvine protein was made by splicing the genes for TSST-1 and TSST-ovine together and then cloning into RN4220.

The G31S/S32P, H135A, Q136A, huvine toxoids, as well as TSST-1, SEC, and native α-toxin and β-toxins were purified by combinations of ethanol precipitation and isoelectric focusing from culture fluids of clones containing the mutated genes. See, Blomster-Hautamaa and Schlievert, *Methods Enzymol* 165:37-43 (11) (1988); and Blomster-Hautamaa et al., *Biochemistry* 25:54-9 (1986). Basically, for production of TSST-1, TSST-1 toxoids, SEC, native α-toxin, and native β-toxin, the organisms were grown overnight in dialyzed beef-heart media. TSST-1, TSST-1 toxoids, SEC, and β-toxin were precipitated from culture fluids with four volumes of absolute ethanol for two days (80% final concentration), resolubilized in distilled water, and then purified by thin-layer isoelectric focusing. Isoelectric focusing pH gradients were pH 3.5-10 for initial separation, followed by gradients of pH 6-8 for TSST-1, TSST-1 toxoids, and α-toxin and pH 7-9 for SEC and β-toxin. Native α-toxin was produced comparably from *S. aureus* strain MNPE, except the toxin was precipitated from culture fluids with 80% final saturation of ammonium sulfate, followed by solubilization in distilled water and three days dialysis, and then followed by isoelectric focusing.

The biologically inactive mutant of α-toxin (H35L) and an enriched preparation of γ-toxin were produced from *E. coli* clones in pET vectors and purified on nickel columns. See Bubeck Wardenburg and Schneewind, *J Exp Med* 205: 287-94 (2008).

TSST-1, TSST-1 mutants, and SEC were homogeneous when tested by sodium dodecyl sulfate polyacrylamide gel electrophoresis (SDS-PAGE) and reversed-phase high-performance liquid chromatography. See Blomster-Hautamaa and Schlievert, 1988, supra. Additionally, these proteins were negative for contaminating lipopolysaccharide (LPS), peptidoglycan, cytolysins, lipase, and proteases. Native α-toxin was further purified by reversed-phase high-performance liquid chromatography and was homogeneous. See, Lin et al., 2011, supra. The α-toxin mutant H35L and γ-toxin, as produced in *E. coli* contained minor *E. coli* contaminates that did not affect experimentation. The purified proteins were quantified by BioRad protein assay.

Example 2

Safety of Toxoid Vaccines in Rabbits

Safety of the toxoids was tested in rabbits (Dutch-belted, purchased from Bakkom Rabbitry, Red Wing, Minn.) by trying to produce TSS in rabbits through administration of the toxoid. Superantigen exotoxins are among the most potent pyrogens known, and amplify the lethal effects of gram-negative lipopolysaccharide LPS by 1,000,000-fold. See Schlievert, *Infect Immun* 36:123-128 (1982). Three assays were used to test for residual toxicity of the toxoids: 1) intravenous administration of toxoids followed by LPS; 2) subcutaneous administration of toxoids via a miniosmotic pump; and 3) an in vitro test of superantigenicity.

Figure 1:
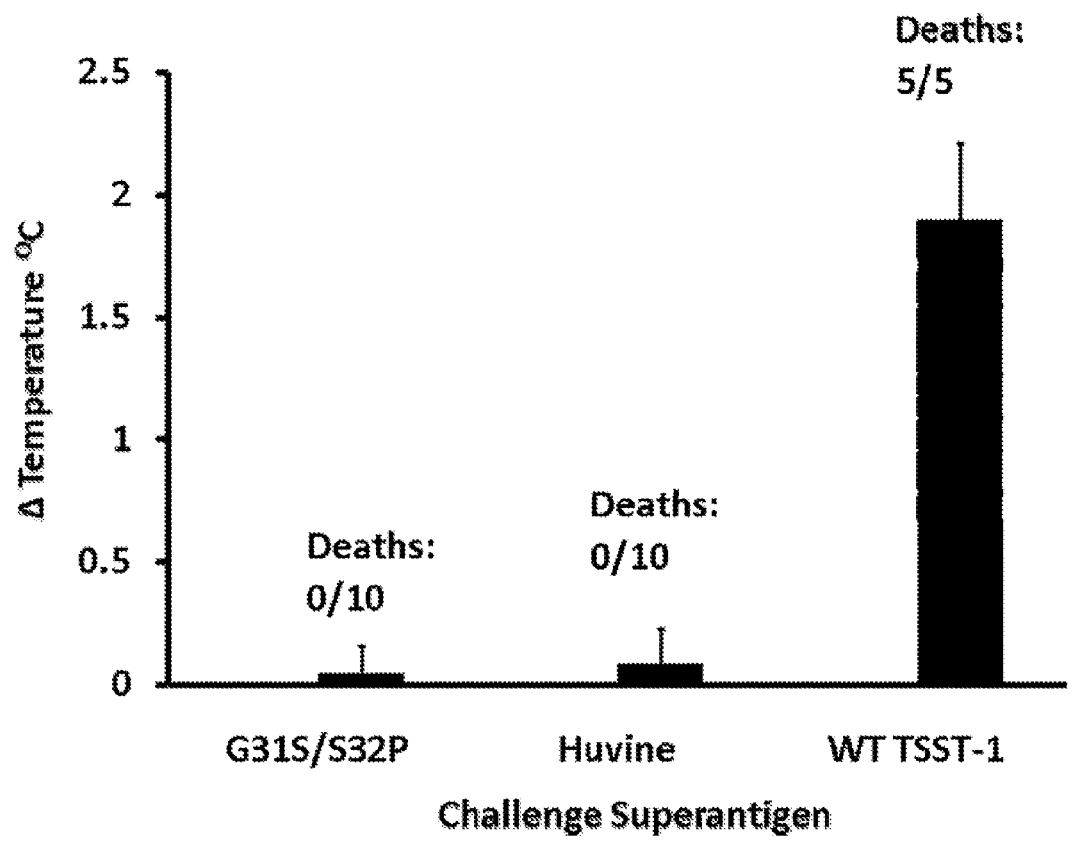

In one experiment, rabbits (10 per group) were challenged IV with a toxoid mutant of TSST-1 (G31S/S32P or Huvine, 1000 µg/kg) or 1 µg/kg of wild-type TSST-1 (5 rabbits). At the 4 hour time point, all rabbits were challenged with 50 µg/kg of LPS (1/10 LD$_{50}$) alone. The LPS was from *Salmonella enteritidis* serovar typhimurium, and prepared by the hot-phenol method. FIG. 1 shows the fever response of the rabbits challenged with the toxoid mutants or the wild-type TSST-1. Neither toxoid induced significant fever over the four-hour time period, whereas wild-type TSST-1 was highly pyrogenic (p<<0.001 for either toxoid versus wild-type TSST-1 by Student's t test). None of the rabbits given 1000 µg/kg of either toxoid followed by LPS succumbed, compared to all five of animals given 1 µg/kg wild-type TSST-1 followed by 50 µg/kg LPS (p=0.003 by Fisher's exact test). These studies indicate both the G31S/S32P and Huvine toxoids are at least 1,000,000-fold inactivated compared to wild-type TSST-1, and both toxoids are well-tolerated by rabbits in that they showed no adverse effects due to the challenge.

Figure 2:
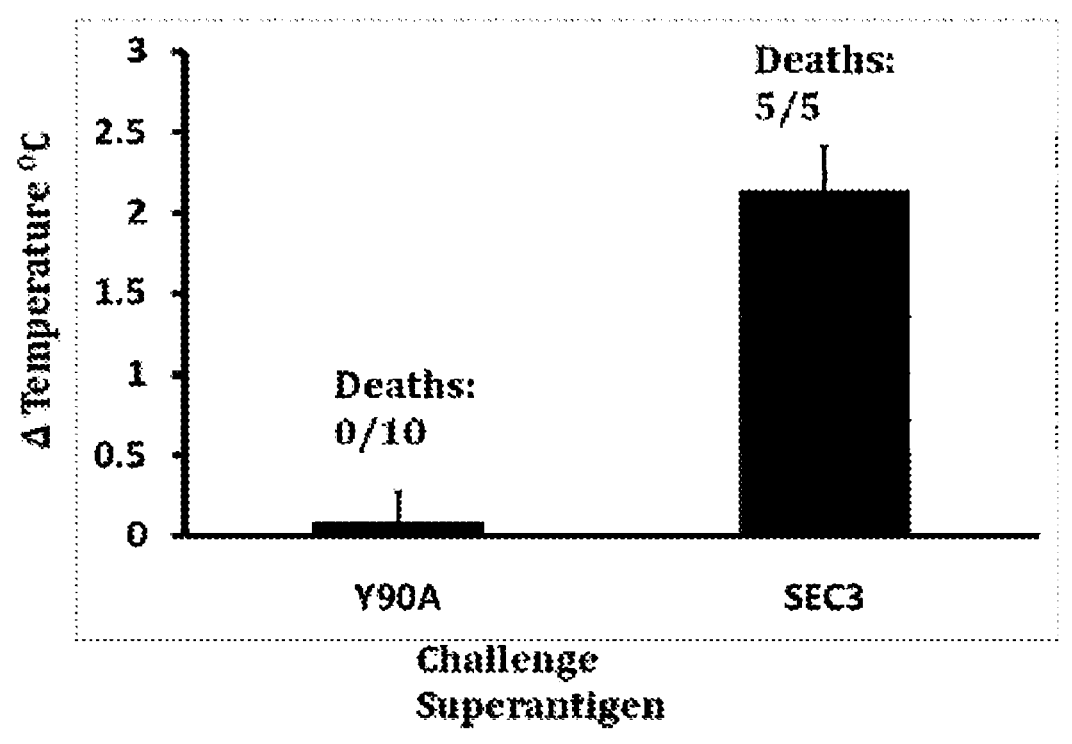

In another experiment, rabbits (5 per group) were challenged IV with 500 µg/kg native TSST-1 or one of the TSST-1 G31S/S32P, H135A, or Q136A mutants, followed by 100 µg/kg of LPS from *Salmonella enteritidis* serovar typhimurium, as prepared by the hot-phenol method at the 4 hr time-point. Fevers were recorded at the 4 hr time-point, just prior to administration of LPS compared to pre-injection of TSST-1 or mutants, and deaths were recorded over a 48 hr time-period. Native TSST-1 caused high fevers, whereas all 3 mutants were non-pyrogenic (p<0.001 for comparison of TSST-1 to any mutant) (FIG. 2). Additionally, all 5 rabbits receiving native TSST-1 followed by LPS, succumbed within 1 hr, but none of the 5 rabbits receiving mutant TSST-1 proteins followed by LPS succumbed by 48 hr (p<0.008 for TSST-1 compared to any mutant) (FIG. 2). These data suggest that all 3 mutant proteins were ≥500.000-fold inactivated, and thus could be considered as toxoids.

A similar experiment was repeated with SEC3 Y90A (staphylococcal enterotoxin C where position 90 is changed from a tyrosine residue to an alanine residue). The results are shown in FIG. 2. As with the G31S/S32P and huvine toxoids, the SEC3 Y90A toxoid is at least 1,000,000-fold inactivated compared to wild-type SEC3 and is well-tolerated by rabbits in that no adverse effects were observed due to the challenge.

TSST-1 alone is lethal to rabbits when administered in subcutaneously implanted miniosmotic pumps; a lethal dose in this model is 75 µg/animal (11 µg/day). Native TSST-1 and each TSST-1 mutant (G31S/S32P, H135A, or Q136A) (1000 µg/animal; 143 µg/day or 10×LD$_{50}$) were administered in miniosmotic pumps (Alza Corporation, Vacaville, Calif.) to 5 rabbits/group. Pumps were implanted while animals were anesthetized with ketamine (25 mg/kg) and xylazine (25 mg/kg) (Phoenix Pharmaceuticals, Burlingame, Calif.). Rabbits were monitored for 7 days for the development of TSS symptoms (fever, diarrhea, reddening of conjunctivae, and evidence of hypotension) and lethal illness, defined as the point 100% predictive of impending death, including simultaneous failure of the animals to remain upright and failure to exhibit flight responses. Animals were euthanized with intravenous injection of 1 ml/kg of Beuthanasia-D (Shering-Plough. Westlake, Tex.). Surviving rabbits were euthanized at the end of 7 days. Administration of the three TSST-1 mutants did not induce fevers, as measured on day 2 post-implantation (p<0.001 for TSST-1 compared to any mutant), did not cause any TSS symptoms, and did not cause deaths in any animals. In contrast, native TSST-1 was pyrogenic, induced TSS symptoms, and caused the deaths of all 5 animals by 48 hr (p<0.008 for TSST-1 compared to any mutant).

Figure 4:
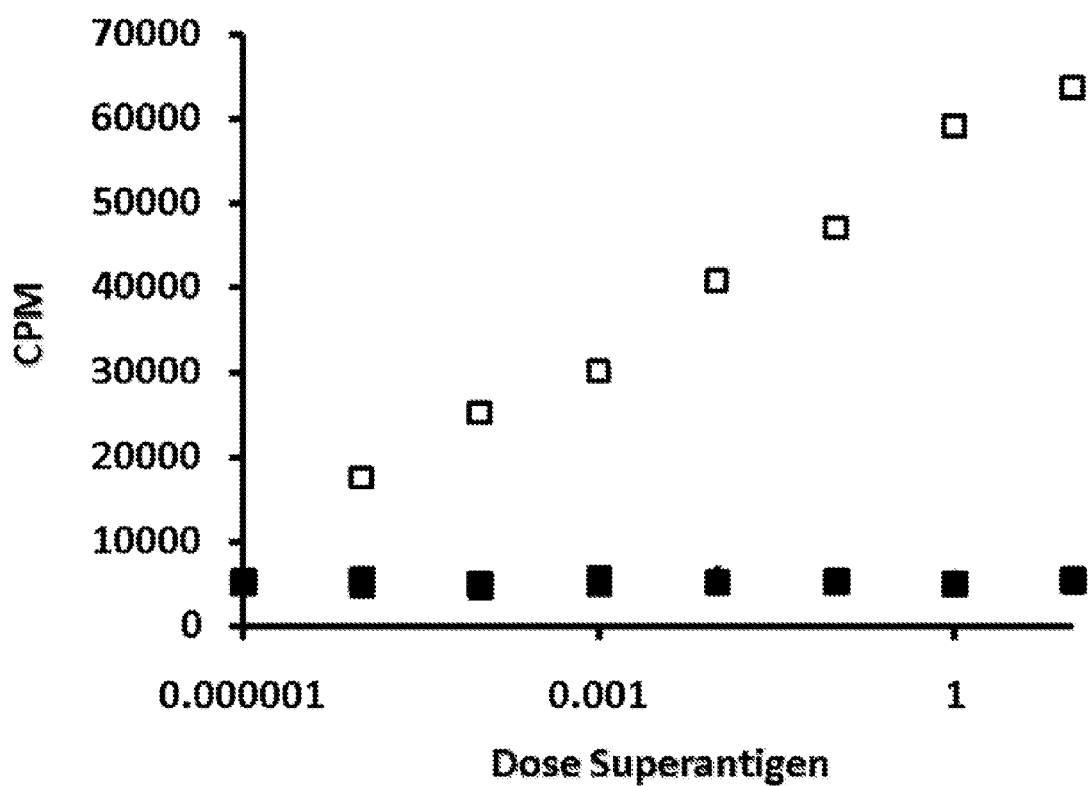
FIG. 4 is a graph showing the superantigenicity of TSST-1 toxoid mutants (G31S/S32P [filled squares], Huvine [filled triangles]) as measured by incorporation of $^3$H-thymidine into DNA of proliferating peripheral blood mononuclear cells (PBMCs). Toxoid and wild-type TSST-1 doses ranged from 10 µg/well to 0.000001 µg/well.

These data were confirmed by in vitro tests that evaluated the ability of the toxoids to cause superantigenic stimulation of human T cells as evaluated by ability to cause proliferation of human PBMCs (FIG. 4). In one experiment, the assay was performed in quadruplicate in 96 well microtiter plates after incubation for four days. See Barsumian et al., *Infect Immun* 22:681-688 (1978). Superantigenicity of wild-type TSST-1 [open squares] was comparably measured. Neither toxoid (G31S/S32P or huvine) exhibited superantigenicity in vitro over the entire dose response (10 µg/well to 0.000001 µg/well), whereas wild-type TSST-1 was superantigenic at doses between 10 µg/well and 0.00001 µg/well (all assays were performed in quadruplicate). See FIG. 4. Counts per minute (CPM) of $^3$H thymidine incorporation into DNA (as a measure of proliferation) was significantly different for both toxoids versus wild-type TSST-1 at all doses from 10 µg/well down to 0.00001 µg/well by Student's t test (P<<0.001). These data confirm that both toxoids were inactivated by at least 10$^6$-fold compared to wild-type TSST-1.

Figure 5:
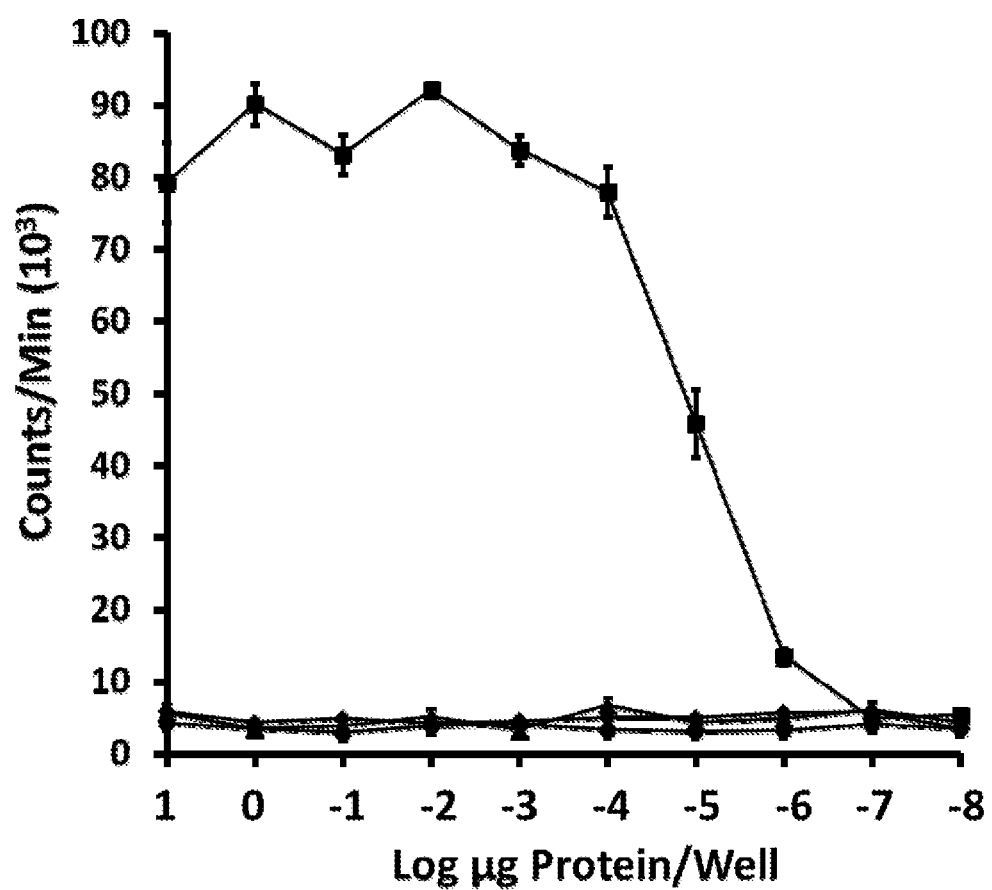
FIG. 5 is a graph showing the superantigenicity±standard deviation of TSST-1 (■), G31S/S32P (♦), H135A (▲), and Q136A (●) for rabbit splenocytes in a 4-day assay. Rabbit splenocytes ($2\times10^5$/well) were incubated with TSST-1 and mutants for 3 days, and then 1 µCi$^3$H-thymidine per well added for 24 hr. DNA was harvested, and counts per minute determined as a measure of T cell proliferation.

In another experiment, rabbit splenocytes (2×10$^5$/well) were incubated with TSST-1 and mutants (G31S/S32P, H135A, or Q136A) for 3 days, and then 1 µCi $^3$H-thymidine per well added for 24 hr. DNA was harvested, and counts per minute determined as a measure of T cell proliferation. See Schlievert et al., *J Infect Dis* 143:509-16 (1981). Native TSST-1 was superantigenic across the toxin range from 10 µg/well down to 10$^{-6}$ µg/well (FIG. 5). None of the 3 TSST-1 mutants exhibited superantigenic activity, even at the 10 µg/well dose. These studies indicate the superantigencity of the mutants was reduced by >10$^7$-fold.

Example 3

Rabbit Antibody Responsiveness

Approximately 20% of people appear unable to develop antibody responses to the superantigen, TSST-1. See Parsonnet, et al., *J Clin Microbiol* 43:4628-34 (2005); and Vergeront, et al., *J Infect Dis,* 148:692-8 (1983). Additionally, menstrual TSS patients, who lack antibodies TSST-1, do not develop protective antibodies following infection and thus are susceptible to multiple recurrences of TSS. See Osterholm, et al., *J Infect Dis* 145:431-40 (1982). This phenomenon is unusual in infectious diseases where typically infection leads to specific immunity. There are two possible mechanisms that have been hypothesized to explain the lack of development of antibodies to TSST-1 in the susceptible individuals: 1) the persons may be genetically unable to recognize TSST-1 as foreign, and thus unable to generate antibody responses to the 22,000 molecular weight protein, and 2) the persons may be hyper-responsive to superantigens, with immune dysregulation preventing antibody responses. If 20% of humans cannot generate antibody responses to any given superantigen through genetic inability, this would weaken an argument to use superantigen toxoids in attempt to vaccinate humans from serious staphylococcal illnesses.

The ability of rabbits to develop protective antibody responses to native TSST-1 was determined as an in vivo model to understand the mechanism for the lack of protective antibody responses in humans. Rabbits, as opposed to mice, are highly susceptible to superantigens and make an excellent model for studying factors important for the development of TSS.

Twenty Dutch-belted rabbits were immunized with 25 µg/dose of native TSST-1 emulsified in incomplete adjuvant every-other-week for three injections. Immunizations were in multiple subcutaneous sites in the nape of the necks. One week after the last immunization of animals, blood was drawn from the marginal ear veins, sera collected, and antibody titers determined by an enzyme-linked immunosorbent assay (ELISA) as described by Strandberg, et al., *J Infect Dis* 202:1690-7 (2010). Briefly, flat-bottomed 96-well plates (NUNC Maxisorp, Portsmouth, N.H.) were coated with 1.0 µg/well of purified native homologous superantigen or cytolysin and then washed. Rabbit serum samples were serially diluted 2-fold beginning with a 1:10 dilution; plates were incubated for a minimum of 1.5 hr at room temperature, and then washed. Horseradish peroxidase-conjugated anti-rabbit IgG antibodies (Sigma-Aldrich, St. Louis, Mo.) were added to the wells. The plates were again incubated for a minimum of 1.5 hr, and the wells were washed. The relative levels of IgG were determined by 100 µl/well addition of an o-phenylenediamine and H$_2$O$_2$ substrate. Colorimetric reactions were halted by the addition of 50 µl of a 12.5% sulfuric acid solution. Plates were scanned for absorbance at 490 nm wavelength using a spectrophotometer.

Immunization with 25 µg/dose of native TSST-1 resulted in only 10/20 rabbits developing antibody titers against TSST-1 and those were >10,000 as tested by ELISA, where titer refers to the reciprocal of the last well dilution to give a positive color change above background. For comparison, humans who are susceptible to TSS have antibody titers of ≤40 against TSST-1, and humans who do not develop TSS have titers of ≥80. Thus, the 10 rabbits that developed antibodies may be considered hyperimmune to TSST-1.

In contrast, the 10 remaining animals had antibody titers of <10, the lower limit of detection with this assay. These 10 non-responsive animals were next continuously immunized monthly for up to 6 months or for as long as they survived. The rabbits were also monitored for development of antibodies to TSST-1 by ELISA monthly. All 10 animals succumbed to the vaccination attempts, with 7 dying after 6 months. At all tested time-points, all of these 10 rabbits had antibody titers of ≤10. Thus, the rabbit model appears to duplicate the human situation in that a significant percentage of both humans and rabbits appear unable to develop antibody responses to TSST-1. The same phenomenon was observed for rabbit antibody responses to the superantigens SEB and SEC.

Example 4

Immunogenicity and Safety of Toxoid Vaccines in Rabbits

Dutch-belted and New Zealand white rabbits were hyperimmunized against biologically inactivated proteins (TSST-1 and α-toxin mutants) by emulsifying 25 µg of each alone or in combination in PBS with an equal volume of Freund's incomplete adjuvant. Immunizations were in multiple subcutaneous sites in the nape of the necks. Native toxins (TSST-1, SEC, α-toxin, β-toxin, and γ-toxin) were used at a dose of approximately 10 µg/ml for immunization following the same protocol. Immunizations for all experiments were every-other-week (days 0, 14, and 28) for three injections. One week after the last immunization of animals, blood was drawn from the marginal ear veins, sera collected, and antibody titers determined by ELISA (see Example 3).

In one experiment, rabbits (20/group) were immunized every-other-week with 25 µg of G31S/S32P or Huvine emulsified in Freund's incomplete adjuvant for three injections subcutaneously in the nape of the neck. The antibody titers of all rabbits one week after the last immunization, as determined by ELISA, were greater than 100,000, compared to <10 for non-immune (20 animals) and pre-immune animals.

Figure 6:
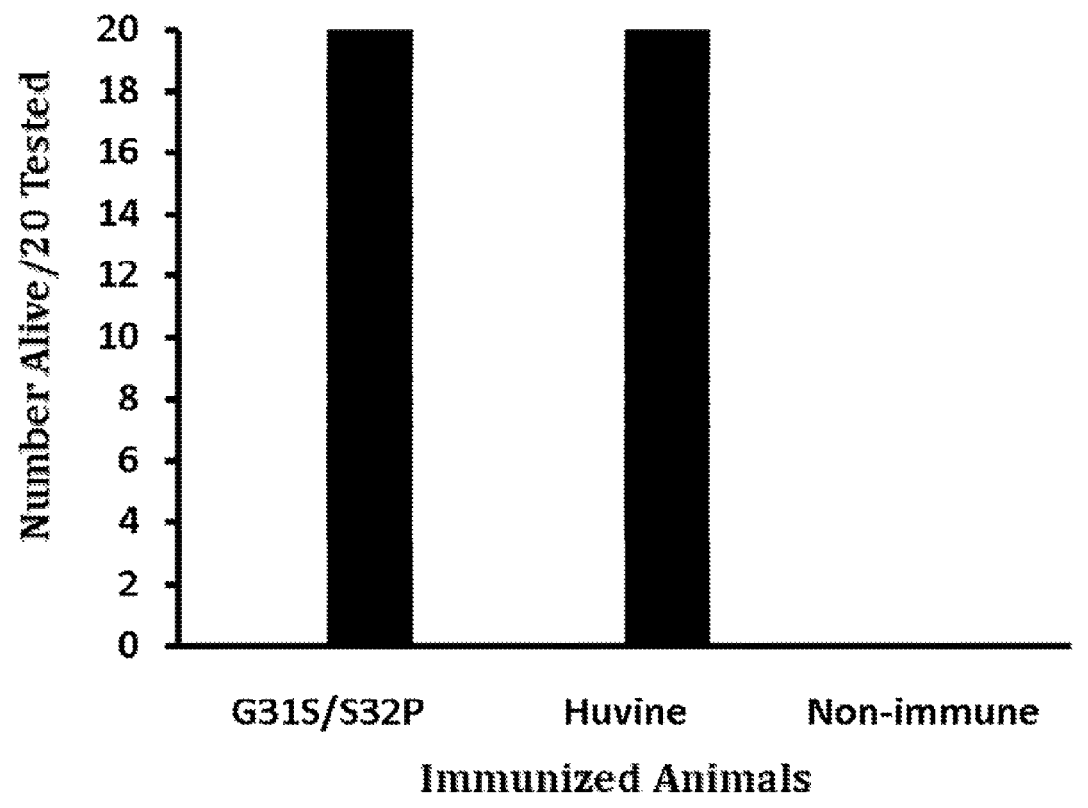

The immunized and non-immunized control animals were challenged with wild-type TSST-1 (500 µg subcutaneously via Alza miniosmotic pump) and monitored for fatal TSS development over a 15 day time period (FIG. 6). Wild-type TSST-1 is lethal to rabbits when administered subcutaneously in Alza miniosmotic pumps. See, Lee et al., *Infect Immun* 59:879-884 (1991). The miniosmotic pumps are designed to release a constant amount of toxin over a 7 day period, during which time rabbits develop uniformly fatal TSS at a wild-type TSST-1 dose of 100 µg/pump (14 µg/day). No LPS is required for lethality in this model.

None of the immunized animals succumbed over the test period, and none developed fevers as measured on day 1 (average 0.3±0.1° C.), none developed diarrhea, and none lost weight. In contrast, all non-immunized animals succumbed (P=7×10$^{-12}$ compared to immunized groups), all had significant fevers on day 1 (average 1.9±0.2° C.), all had profuse diarrhea, and all lost weight prior to their deaths.

Figure 7:
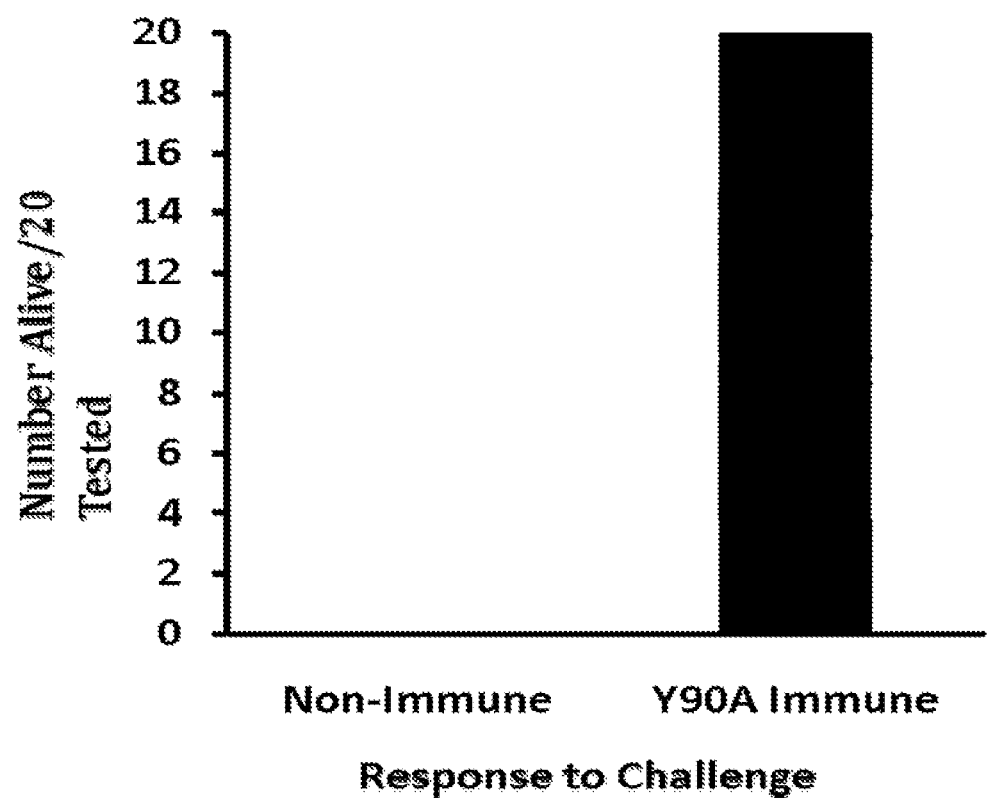
FIG. 7 is a bar graph indicating the number of alive rabbits (prior immunization with a toxoid or non-immunized) after challenge with wild-type SEC3. Prior immunization with SEC3 Y90A protected rabbits from SEC3 lethality. Animals were monitored 15 days for health.

A similar experiment was repeated using the SEC3 Y90A toxoid. As shown in FIG. 7, prior immunization with SEC3 Y90A protected rabbits from challenge with wild-type SEC3.

In another experiment, rabbits (10/group) were immunized three times, every-other-week, with the TSST-1 mutants G31S/S32P, H135A, or Q136A. Upon drawing blood one week after the third injection, all 10 animals in each group (30 total) had antibody titers of >10,000 against native TSST-1 as tested by ELISA. These data indicate the prior failure of 50% of rabbits to develop antibody responses resulted from TSST-1 induced dysregulation of immune responses, rather than genetic inability to recognize TSST-1 as a foreign protein.

The rabbits immunized against TSST-1 mutants G31S/S32P, H135A, or Q136A and control, non-immunized animals (5/group) then were challenged one week after the last immunization with otherwise lethal doses of native TSST-1, either (10 µg/kg) plus LPS (10 µg/kg) intravenously (5000× LD$_{50}$) or alone (500 µg/kg) in miniosmotic pumps (71 µg/day; 5.5×LD$_{50}$). None of the 5 rabbits per group developed fevers when challenged with TSST-1 in the LPS enhancement model, and none of the 5 animals/group succumbed after being given LPS at the 4 hr time-point. In contrast, all 5 control, non-immunized animals developed TSST-1 induced fevers, and all succumbed in <6 hr post-administration of LPS. In the miniosmotic pump model, none of the 5 animals/group developed fevers, as measured on day 2 post-implantation, none showed TSS symptoms, and none succumbed. In contrast, all 5 control, non-immunized animals showed fevers, and all succumbed by 2 days post-implantation.

Collectively, Examples 2 and 4 indicate the toxoids are safe in that the proteins are >10$^6$ inactivated; the toxoids are immunogenic (titers >100,000 by three immunizations, compared to <10 for pre-immune and control animals); and the animals were protected in the standard highly sensitive rabbit model of TSS when challenged with 5× the dose of TSST-1 to cause 100% lethality.

Example 5

TSST-1 Neutralization by Antibodies

Figure 8:
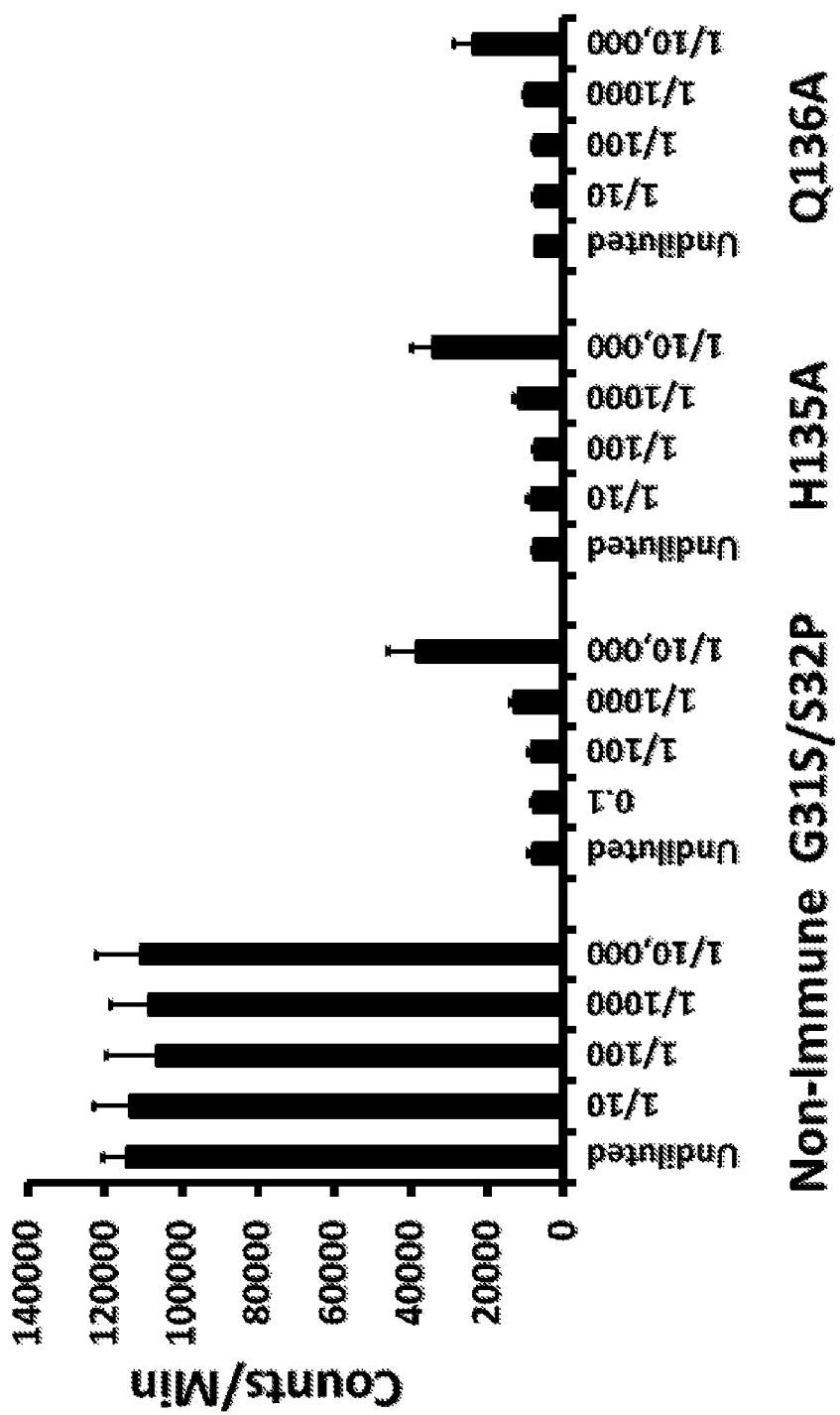
FIG. 8 is a bar graph comparing the superantigenicity of TSST-1 (1 µg/well), in pooled rabbit sera from non-immune animals versus animals hyperimmune to TSST-1 mutants G31S/S32P, H135A, and Q136A, as tested in a 4 day assay with rabbit splenocytes. Splenocytes were incubated with designated dilutions of sera+TSST-1 for 3 days, and then 1 µCi$^3$H-thymidine was added for 24 hr. DNA was harvested and counts/min determined as a measure of lymphocyte proliferation. Counts/min splenocytes+TSST-1=110, 801±8647. Counts/min splenocytes alone=7248±1164.

Prior to their challenge with native TSST-1, sera collected from the 10 rabbits above that were immunized three times every-other-week with the mutant proteins (G31S/S32P, H135A, or Q136A) were pooled. These pooled sera and pooled sera from pre-vaccinated animals were tested in vitro for ability to neutralize TSST-1 superantigenicity, as tested with rabbit splenocytes and 1 µg/well of native TSST-1 (FIG. 8). In these assays, undiluted and 1/10 and 1/100 diluted sera from immune animals completely neutralized TSST-1 superantigenicity; even 1/1000 diluted pooled sera from immune animals partially neutralized native TSST-1 superantigenicity. In contrast, 20 µl of undiluted, pre-immune pooled serum failed to neutralize superantigenicity Inhibition of superantigenicity of TSST-1 at all dilutions of immune sera was at least significantly different from inhibition of superantigenicity with non-immune sera at p<0.003. The data suggest the mechanism of immunizing against TSST-1 lethality is neutralization of superantigenicity.

Example 6

Immunization Against Fatal Pneumonia

Figure 9A:
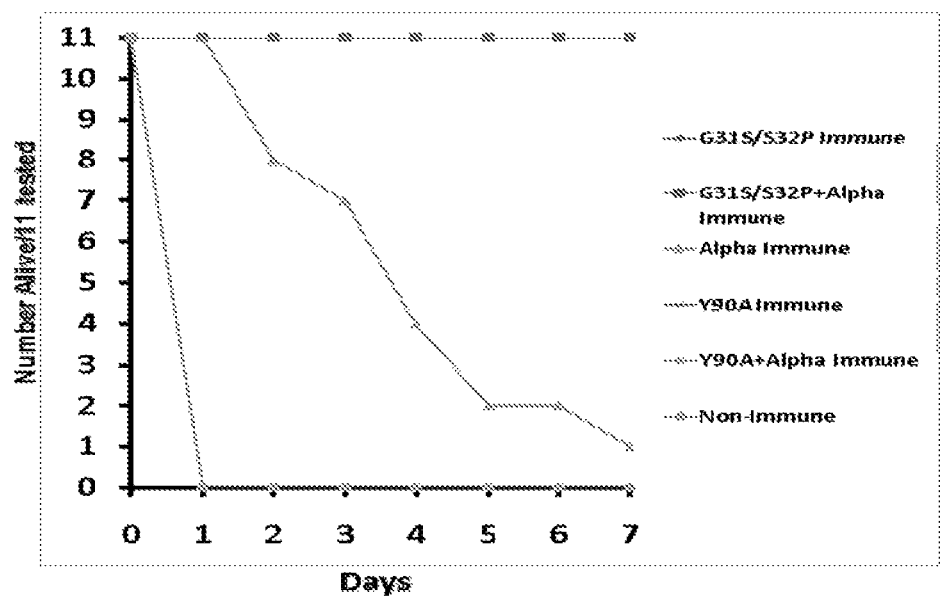
FIG. 9A is a line graph showing the number of pre-immunized or non-immunized rabbits alive after challenge with wild-type USA200 MNPE (for those immunized with G31S/S32P, G31S/S32P+Alpha, or Alpha alone) or USA400 MW2 (for those immunized with Y90A and Y90A+Alpha toxoid) intra-bronchially with $2\times10^9$ bacteria per animal. The animals were monitored for 7 days for health. Prior immunization with G31S/S32P, Y90A±Alpha toxoid protected rabbits from lethal pneumonia.

Rabbits (11 per group) were immunized against G31S/S32P TSST-1 and alpha toxin, and separately with Y90A SEC3 and alpha toxin. Additionally, studies were performed comparably with G31S/S32P alone, Y90A SEC3 alone, and alpha toxin alone. All animals were immunized every-other-day with 25 μg of each antigen/toxoid for three injections in Freund's incomplete adjuvant. One week after the last immunization, ELISA was performed. The immunized rabbits had antibody titers in excess of 100,000 compared to <10 for pre-immune and non-immune animals. The rabbits were then challenged intra-bronchially with $2 \times 10^9$ colony forming units (CFUs) USA200 stain MNPE (for those animals immune to TSST-1 and alpha toxoids) or $2 \times 10^9$ CFUs USA400 strain MW2 (for animals immune to SEC3 and alpha toxin). Rabbits were monitored for 7 days for protection from challenge compared to control, non-immune animals (FIG. 9A).

Animals immunized against G31S/S32P alone or in combination with alpha toxin were completely protected from challenge with USA200 MNPE *S. aureus*; those animals immunized with alpha toxin alone were only partially protected. For immunized animals, except for those rabbits immunized against alpha toxin alone, none of the animals showed fevers, diarrhea or lost weight over the 7 day period; all remained healthy. These data with alpha toxin differ from studies performed in mice, where complete protection was seen upon vaccination with alpha toxin alone. Mice are unlike humans in regard to *S. aureus* infections, whereas rabbits are highly similar to humans, so the rabbit is the more sensitive animal model. Rabbits immunized against Y90A SEC alone or Y90A+alpha toxin were completely protected from challenge with USA400 MW2. Nonimmune animals (shown only as one line in this study) all succumbed in 1 day when challenged with either USA200 MNPE or with USA400 MW2.

In another experiment, a rabbit pulmonary illness model was used in which Dutch-belted rabbits were administered MNPE ($2 \times 10^9$ CFU in 0.2 ml volumes) via intra-tracheal inoculation as described by Strandberg, et al., *J Infect Dis* 202:1690-7 (2010). Briefly, rabbits were anesthetized with subcutaneous injections of ketamine (25 mg/kg) and xylazine (25 mg/kg) (Phoenix Pharmaceuticals, Burlingame, Calif.). Their necks were shaved, and small incisions were made to expose the tracheas. Small (3 mm) incisions were made into the tracheas before inserting 1 mm diameter polyethylene catheters (Becton, Dickinson, and Co, Sparks, Md.) and threading them into the left bronchi. MNPE was administered through the catheters, and then catheters removed and incision sites closed. Rabbits were monitored for 7 days for the development of TSS symptoms (fever, diarrhea, reddening of conjunctivae, and evidence of hypotension) and lethal illness, defined as the point 100% predictive of impending death, including simultaneous failure of the animals to remain upright and failure to exhibit flight responses. Animals were euthanized with intravenous injection of 1 ml/kg of Beuthanasia-D (Shering-Plough. Westlake, Tex.). Surviving rabbits were euthanized at the end of 7 days.

Figure 9B:
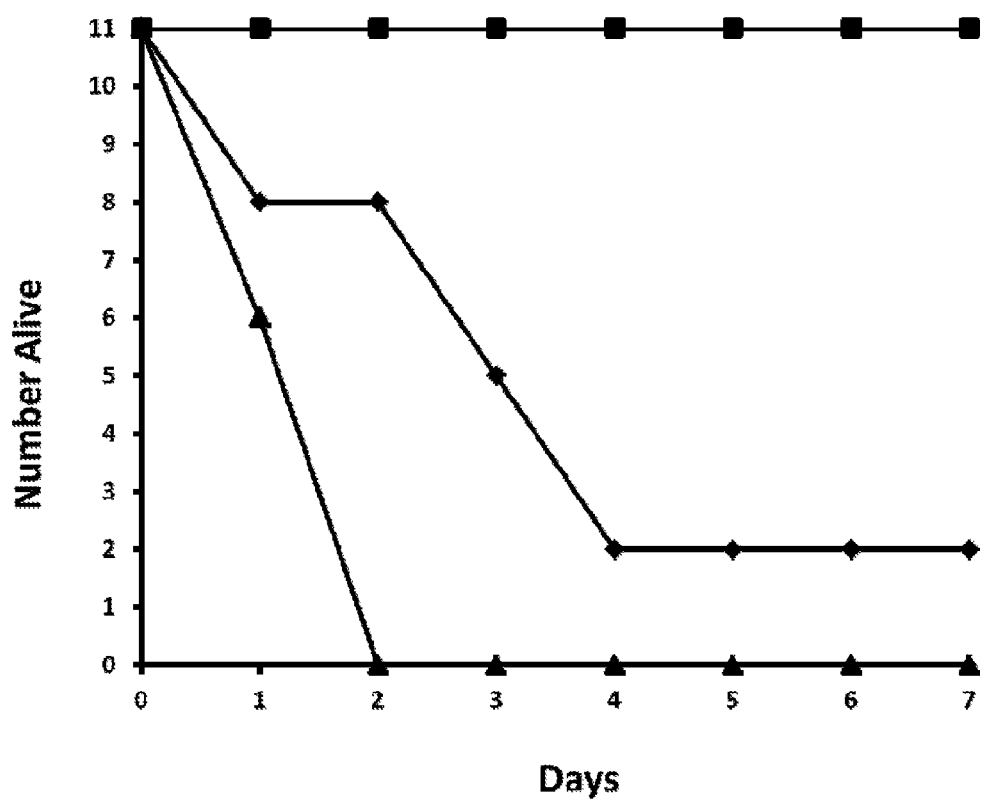
FIG. 9B is a line graph showing the number of pre-immunized or non-immunized rabbits alive after challenge with wild-type USA200 MNPE. Rabbits (11/group) were immunized three times with antigens, TSST-1 (G31S/S32P)+SEC+α-toxin (H35L or wild-type) as a cocktail (□) or α-toxin (H35L) alone (♦), or remained non-immunized (▲). Antigens were emulsified in incomplete adjuvant and immune animals plus non-immune control animals challenged intrapulmonary with 2×10$^9$ S. aureus MNPE. Rabbits immunized against TSST-1 (G31S/S32P)+SEC+α-toxin (H35L or wild-type) were significantly protected from lethality compared to non-vaccinated animals or animals vaccinated against α-toxin (H35L or wild-type) alone (p<0.001). Animals vaccinated against α-toxin (H35L or wild-type) were significantly delayed in lethality compared to non-vaccinated controls (p=0.001).

The ability of a trivalent vaccine composed of TSST-1 (G31S/S32P), a low dose of native SEC, and a non-toxic dose of α-toxin (H35L) (5 rabbits) or wild-type α-toxin (6 rabbits) to protect from lethal pneumonia with a high dose challenge with USA200 *S. aureus* MNPE ($2 \times 10^9$ CFUs) was evaluated. Immunization against the non-toxic mutant of α-toxin (H35L) (5 animals) or native α-toxin (5 animals) alone to protect rabbits from similar challenge with *S. aureus* MNPE also was evaluated. All animals were immunized every-other-week for 3 injections in incomplete adjuvant, shown to have high antibody titers (>10,000) against all three native toxins by ELISA, and were challenged intra-pulmonary one week after the last immunization, along with non-immune controls, with $2 \times 10^9$ MNPE. There were significant differences in survivals among the groups (p<0.001). For rabbits immunized against the trivalent vaccine containing TSST-1 G31S/S32P+SEC+α-toxin (H35L or native), all were protected from lethal pneumonia (FIG. 9B). In contrast, all 11 non-immunized animals succumbed to the lethal challenge (p<0.001). Rabbits immunized with the α-toxin H35L alone or native α-toxin alone showed delayed deaths due to challenge with MNPE, but ultimately, 9/11 succumbed (p=0.001, compared to non-immunized controls). Rabbits immunized against the trivalent vaccine had better survival than rabbits immunized against α-toxin (H35L or native) alone (p<0.001).

Example 7

Pentavalent Vaccine Prevents Infective Endocarditis and Sepsis

Protection of rabbits from USA200 MNPE sepsis and infectious endocarditis was assessed by immunization with (i) G31S/S32P TSST-1, Y90A SEC, alpha toxoid, beta toxin, and gamma toxin or (ii) G31S/S32P TSST-1, SEC, alpha toxoid (H35L), beta toxin, and gamma toxin. USA200 MNPE secretes all of these exotoxins. In this model, New Zealand white rabbits have their left carotid valve damaged by a 2 hour catheterization. See, Schlievert, et al., *Infection and Immunity* 66(1):218-23 (1998). Briefly, the rabbits were anesthetized with ketamine (25 mg/kg) and xylazine (25 mg/kg). Incisions were made on the left side of the necks to expose the left common carotid arteries. Catheters were inserted into the left carotid arteries and threaded until against the aortic valves, where they remained in place for 2 hr to induce damage to the endothelia. After 2 hr, the catheters were removed and the surgical sites closed. Doses of $2 \times 10^8$ CFUs of *S. aureus* USA200 MNPE were injected into the marginal ear veins. Because the animals were injected intravenously, progression to lethal sepsis can be monitored as well as infective endocarditis. Rabbits were monitored for 4 days for signs of illness and lethality, as described above. At the time of impending death or after 4 days, rabbits were euthanized. Hearts were removed and examined for vegetations. If vegetations were observed, they were excised, weighed, homogenized and serially diluted to determine CFUs. If vegetations were not present, scrapings of the aortic valves were taken, serially diluted, and plated.

Figure 10A:
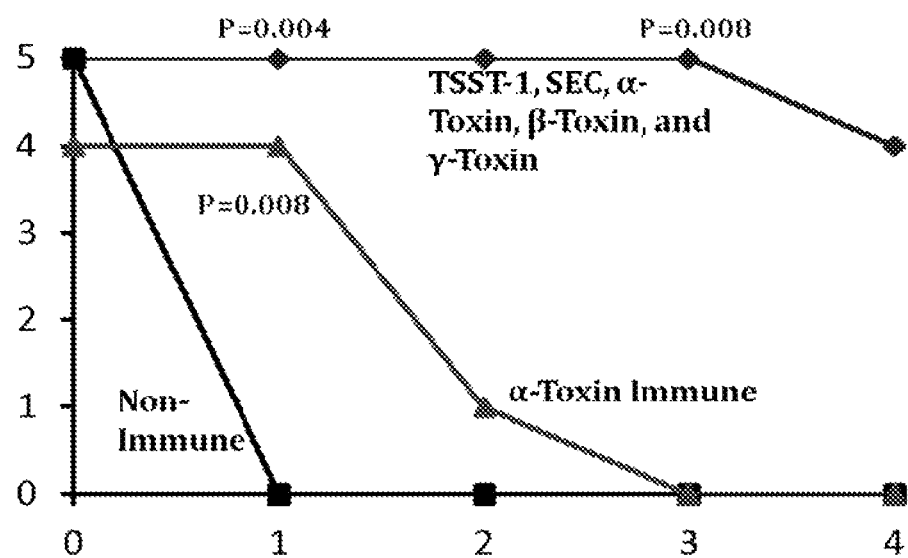
FIG. 10A is a line graph showing the number of pre-immunized or non-immunized rabbits (4-5 per group) alive after challenge with wild-type USA200 MNPE IV with 2×10$^8$ bacteria per animal. The pre-immunized animals were immunized with G31S/S32P+Y90A+Alpha+Beta+Gamma or alpha toxoid alone. The health of the rabbits was monitored for 4 days.

In one experiment, rabbits immunized with the combinations of superantigen toxoids and cytolysins (G31S/S32P, Y90A SEC, H35L alpha toxoid, wild type beta toxin, and gamma toxin) were completely protected from lethal sepsis and formation of infectious endocarditis vegetations (FIG. 10). The one immunized rabbit that died succumbed to lethal anaphylaxis 30 seconds after receiving buprenorphine pain-relieving medication. The remaining animals remained healthy for the 4 day test period (corresponds to the peak time for formation of cardiac vegetations, the hallmark sign of endocarditis). Some rabbits were immunized against alpha toxin only, and these animals showed delayed deaths. Non-immune animals succumbed in 1 day.

Figure 10B:
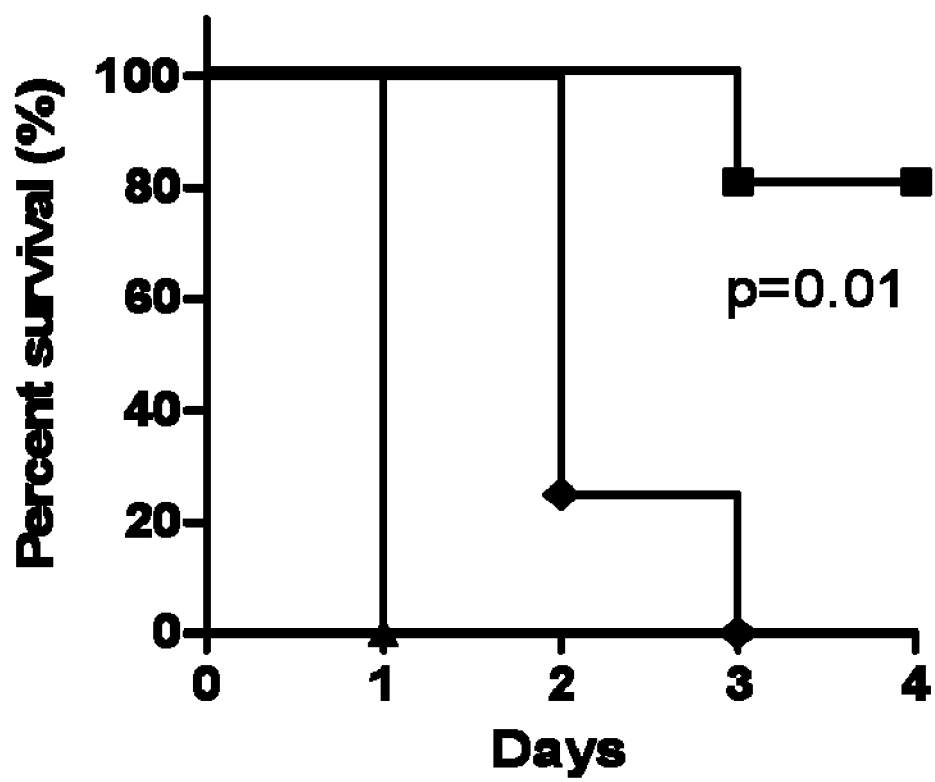
FIG. 10B is a line graph showing the number of pre-immunized or non-immunized rabbits (4-5 per group) alive after challenge with wild-type USA200 MNPE IV with 2×10$^8$ bacteria per animal Rabbits were immunized three times with TSST-1 (G31S/S32P), SEC, α-toxin (H35L), β-toxin, and γ-toxin (■) or α-toxin (H35L) alone (♦), or remained non-vaccinated (▲). Challenge organism was intravenous USA200 S. aureus MNPE (2×10$^8$/2 ml volume in PBS)

In another experiment, rabbits (4-5/group) were immunized against G31S/S32P TSST-1, SEC, alpha toxoid (H35L), beta toxin, and gamma toxin or alpha-toxoif H35L alone every-other-week for 3 injections. Control animals remained non-immunized. After immunization, all animals were highly immune to each toxin by ELISA, and then all immune plus non-immunized animals were challenged one week after the last immunization with MNPE in the model of infective endocarditis and sepsis described above. Rabbits previously immunized with the pentavalent vaccine were significantly protected from lethal sepsis (FIG. 10B). Vegetation sizes for MNPE are typically up to 100 mg (data not shown). One rabbit from the pentavalent immunized group died late on day 2 and had a vegetation of 6 mg with $1 \times 10^8$ CFU. The largest vegetation seen in the immunized rabbits was 14 mg while the smallest was 1 mg, vastly smaller than the typical size associated with MNPE. The data suggest that prior immunization against these 5 secreted toxins provided immune protection against otherwise lethal challenge and significantly reduced vegetation size.

For rabbits previously immunized against α-toxin H35L alone, three of four developed small vegetations (2-3 mg), and all succumbed from lethal sepsis (FIG. 10B), though lethality was delayed compared to the non-immunized control group (day 2 or 3 for H35L immunized rabbits versus day 1 for control rabbits). There were significant differences in overall survival among the groups (p=0.01). The survivals of animals immunized against α-toxin alone and pentavalent vaccine were both significantly better than non-immunized animals (p=0.002 and 0.001, respectively). Furthermore, rabbits immunized against pentavalent vaccine were also significantly protected from lethal sepsis than rabbits immunized against α-toxin alone (p=0.004).

All control, non-immunized animals in this study succumbed to lethal sepsis by 24 hr post injection of MNPE (FIG. 10B). None of the animals had significant vegetations, presumably due to the rapidity with which the animals succumbed, though there was visual confirmation of small vegetations forming on their aortic valves.

Example 8

Figure 11:
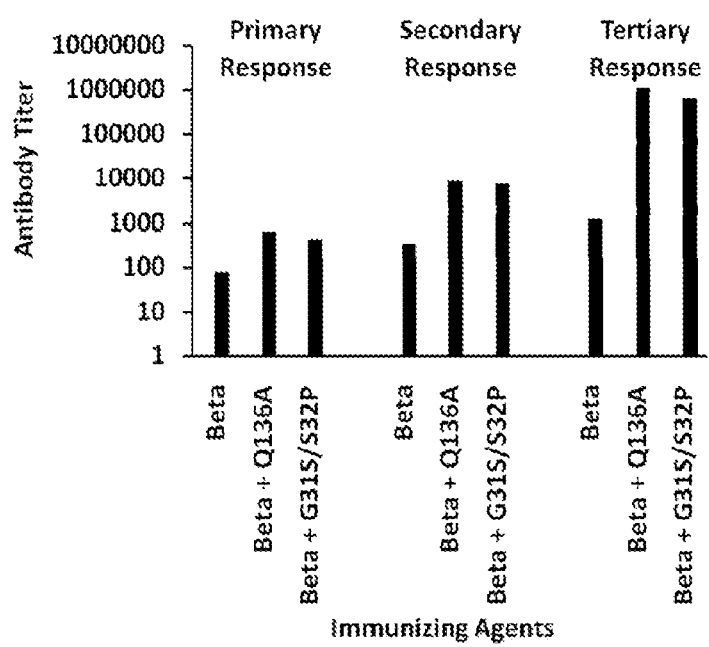
FIG. 11 is a bar graph showing the antibody titer of Dutch-belted rabbits (3/group) in response to immunization with S. aureus β-toxin (beta) alone and in combination with two toxoids of TSST-1: TSST-1 (Q136A) and TSST-1 (G31S/S32P). Immune responses in the presence of TSST-1 mutants, compared to responses to β-toxin alone were significantly different (p<0.01) by Student's t test.

TSST-1 (Q136A) and TSST-1 (G31S/S32P) Function as Adjuvants to Stimulate Antibody Responses to Other Antigens Rabbits immunized with either TSST-1 mutant (G31S/S32P or Q136A) in combination with the staphylococcal cytolysin β-toxin developed much higher antibody responses to β-toxin than rabbits immunized with β-toxin alone (FIG. 8). Rabbits were immunized three times with an immunizing dose of all proteins of 25 μg/rabbit, and then antibody titers were assayed one week after immunization. Assessment of primary immune response by ELISA was on day 14 after day 0 immunization in incomplete adjuvant; secondary immune response by ELISA on day 28 after day 14 immunization in incomplete adjuvant; and tertiary immune response by ELISA on day 42 after day 28 immunization. Rabbits immunized with β-toxin alone developed immune response antibody titers that increased from 100 after the first immunization to 600 after the third immunization (FIG. 11). In contrast, co-immunization with β-toxin and either TSST-1 (G31S/S32P) or TSST-1 (Q136A) resulted in antibody titers to β-toxins increasing from 200- 300 after the first immunization to nearly $10^6$ after the third immunization (p<0.001 comparing antibody titers after the third immunization with β-toxin alone versus co-immunization with β-toxin+either TSST-1 mutant). These data indicate that the MHC II mutant TSST-1 (G31S/S32P) and the TCR mutant TSST-1 (Q136A) function as effective adjuvants. Thus, SAgs possess inherent adjuvant activity in that they highly significantly synergize with other antigens to amplify antibody responses. This experiment was repeated with use of sheep erythrocytes and ovalbumin plus/minus mutant TSST-1 proteins with similar results.

Example 9

TSST-1 Binds to CD40

Superantigens (SAgs) are potent T lymphocyte mitogens, a property referred to as superantigenicity, and stimulate T lymphocytes from a variety of species. However, SAgs do not produce TSS in mice or most non-human primates, but they induce TSS in humans, and rabbits and ferrets as animal models. Thus, the vaccination studies described herein were performed in rabbits because these animals, like humans, are highly susceptible to the toxic effects of superantigens. However, studies in rabbits restrict the ability to determine the mechanism of adjuvanticity. Because of this problem, in vitro studies were performed with human vaginal epithelial cells (HVECs) to determine possible mechanisms of intrinsic adjuvanticity. T cell stimulation is dependent on SAgs binding the variable part of the β-chain of the T cell receptor (Vβ-TCR), and does not depend on the antigen specificity of the T cells. In addition, presentation of SAgs to T cells by MHC class II molecules is required for optimal T cell stimulation. Presentation occurs by SAgs binding invariant regions of MHC II molecules on the surface of macrophages in the absence of antigen processing. SAgs do not bind in the typical groove area of the TCR, which is involved in antigenic peptide-MHC class II recognition. Rather, the toxins interact with external, relatively invariant sites on Vβ-TCRs. T cell stimulation (primarily CD4+) and macrophage activation by SAgs contribute significantly to the development of TSS illnesses through cytokines, including IL-1β, IL-2, TNF-alpha, TNF-beta, and interferon gamma.

Prior studies examined changes in HVEC gene expression following exposures to TSST-1 by microarray analysis. Peterson et al., *Infect Immun* 73:2164-74 (2005). In addition to increasing the expression of cytokines and chemokines, CD40 RNA transcription was up-regulated when ATCC HVECs were incubated with TSST-1 (unpublished data). CD40 is present on epithelial cells and antigen-presenting cells, including B lymphocytes. CD40 is an important immune co-stimulatory molecule required for optimal production of antibodies by B cells. See Elgueta et al., *Immunol Rev* 229:152-72 (2009). CD40 also facilitates immunoglobulin isotype class switching. Additionally, HVECs lack MHC II molecules on their surfaces (data not shown). Thus, these cells were used to determine if TSST-1 interacts with CD40 as the potential receptor needed for adjuvanticity.

The ability of TSST-1 to bind to CD40 was assessed in Western immunoblots. CD40 (2 μg, from R&D systems) and control protein (ovalbumin, 2 μg) was subjected to non-denaturing PAGE and transblotted onto a polyvinylidene fluoride (PVDF) membrane. Membranes were blocked by addition of 1% bovine serum albumin and 1% human serum for 30 min. Subsequently, 0.033 μg/ml to 33 μg/ml of TSST-1, TSST-1 (Q136A), or TSST-1 (G31S/S32P) were incubated with the membranes for 24 hr at room temperature. The membranes were then washed and incubated successively with rabbit antibodies against TSST-1, alkaline phosphatase-conjugated antibodies against rabbit IgG, and finally substrate, with washing between steps.

Binding of TSST-1 to CD40 was observed. Similar binding to CD40 occurred with two toxoid mutants of TSST-1, G31S/S32P, which lacks ability to bind to MHC II molecules, and Q136A, which lacks ability to bind to Vβ-TCR. The two toxoid mutants did not bind to electrophoresed ovalbumin. The binding of all three TSST-1 proteins appeared comparable. The comparable binding of all three proteins indicates that regions of TSST-1 that interact with Vβ-TCR (Q136) and α-chain MHC II (G31/S32) do not interact with CD40.

To determine the Kd for TSST-1 binding to CD40, various concentrations of TSST-1, ranging from 0.033 µg/ml to 33 µg/ml, were incubated individually with 2 µg CD40 on PVDF membranes overnight to ensure equilibrium in binding. Subsequently, the membranes were washed and incubated successively with rabbit antibodies against TSST-1, alkaline phosphatase-conjugated antibodies against rabbit IgG, and finally substrate. The density of protein bands was compared to standard amounts of purified TSST-1 treated similarly, with concentrations compared by NIH program ImageJ (world wide web at rsbweb.nih.gov/ij/). The Kd of the interaction of CD40 with TSST-1 was approximately $2.7 \times 10^{-6}$ M as determined by Scatchard analysis.

In order to have an independent method to assess CD40 interaction with TSST-1, pull-down assays were used to confirm binding. Magnetic beads (Dynabeads, Invitrogen Life Sciences, Grand Island, N.Y.) coated with protein A were treated with goat IgG antibodies against TSST-1, then TSST-1, and finally CD40 (2 ug), with washing between steps and after incubation with CD40. The resultant preparations were treated with sodium dodecyl sulfate (SDS) PAGE sample buffer, electrophoresed by SDS-PAGE, and then tested by Western immunoblotting for CD40. Controls consisted of treating the beads without TSST-1 but with CD40. In the presence of TSST-1 on the beads, more CD40 was pulled down than in the absence of TSST-1, confirming that TSST-1 bound to CD40.

Figure 12:
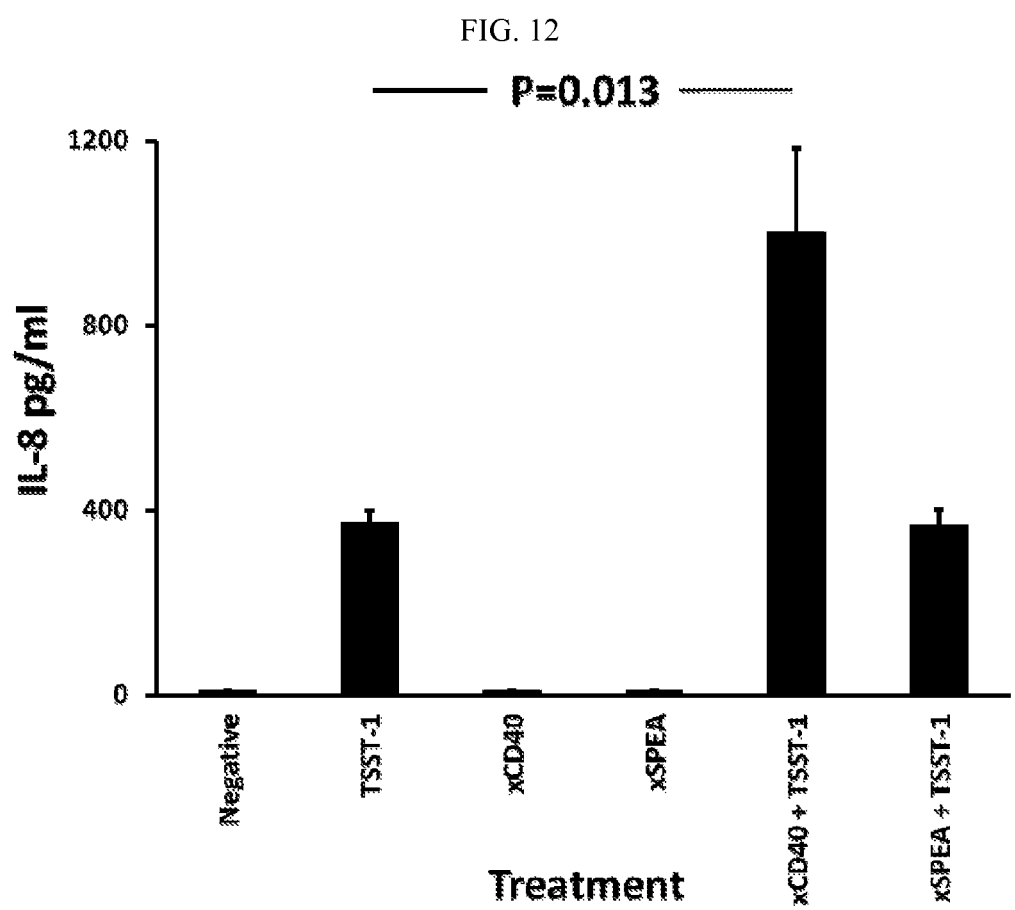
FIG. 12 is a bar graph showing IL-8 production (pg/mL) from HVECs treated with TSST-1 and monoclonal antibodies against CD40 that neutralize interaction with T cell CD40 ligand. Monoclonal antibodies against CD40 alone (xCD40; 20 µl undiluted), TSST-1 alone (100 µg/ml), isotype-matched monoclonal antibodies against streptococcal pyrogenic exotoxin A (xSPEA) and monoclonal antibodies against CD40+TSST-1, and monoclonal antibodies against streptococcal pyrogenic exotoxin+TSST-1 were incubated with confluent HVECs in 96 well microtiter plates in triplicate for 6 hr. Subsequently IL-8 production was measured by ELISA. Bars represent standard error of the means.

It was hypothesized that co-incubation of TSST-1 and monoclonal antibodies that neutralize CD40 interaction with CD40 ligand on T cells with HVECs would result in interference with IL-8 chemokine production. HVECs from a pre-menopausal woman were described by Petersen et al., 2005, supra. A second HVEC line was purchased from ATCC (Accession No. CRL-2614). HVECs were cultured in keratinocyte serum-free medium (KSFM) with antibiotics until 24 hr before use. At that time, the cells were changed to KSFM without antibiotics. Experiments were performed in KSFM medium without antibiotics. Unexpectedly, a nearly 3-fold synergy in IL-8 chemokine production was observed when both TSST-1 and monoclonal antibodies against CD40 were incubated with the HVECs compared to TSST-1 alone (FIG. 12); the monoclonal antibodies to CD40 did not induce cytokine production. Additionally, an irrelevant monoclonal antibody (monoclonal antibodies against streptococcal pyrogenic exotoxin A (SPEA) did not synergize with TSST-1 to cause amplified IL-8 production. Finally, the same monoclonal antibodies against CD40 block CD40 ligand stimulation of chemokine production from HVECs (data not shown).

Collectively, these data suggest that TSST-1 binds to the immune co-stimulatory molecule CD40, which is required for optimal stimulation of B cell to produce neutralizing antibodies, thus accounting for the TSST-1 mutant toxoid adjuvanticity. It is likely that native TSST-1 interacts more prominently with MHC II and Vβ-TCR to mask the adjuvant effect.

Example 10

Immunization Against Necrotizing Pneumonia

Protection of rabbits from necrotizing pneumonia resulting from infection with USA400 strains MW2 and c99-529 was assessed by immunization with alpha toxin, SEC, and SEB. MW2 is positive for production of the cytolysin alpha toxin and SEC, and strain c99-529 is positive for alpha toxin and SEB.

Rabbits (10 per group) were immunized against alpha toxin and SEC by three injections subcutaneously in the nape of the neck with injections combinations as follows: Day 0 (10 µg alpha toxin, 10 µg SEC, and 10 µg SEB) emulsified in Freund's incomplete adjuvant (Difco, Detroit, Mich.); Day 14 (10 µg alpha toxin, 10 µg SEC, and 10 µg SEB) emulsified in Freund's incomplete adjuvant (Difco, Detroit, Mich.); and Day 28 (10 µg alpha toxin, 10 µg SEC, and 10 µg SEB) emulsified in Freund's incomplete adjuvant (Difco, Detroit, Mich.). Rabbit serum antibody titers against the respective toxins were demonstrated to be >10,000 by ELISA.

Four groups of rabbits were challenged intra-pulmonary with $2 \times 10^9/0.2$ ml volume of either MW2 or c99-529. The four groups of rabbits were:
  Group 1: 10 rabbits that were alpha toxin+SEC immune and challenged with MW2; Group 2: 10 rabbits that were non-immune and challenged with MW2; Group 3: 10 rabbits that were alpha toxin+SEB immune and challenged with c99-529; and Group 4: 10 rabbits that were non-immune and challenged with c99-529

Figure 13:
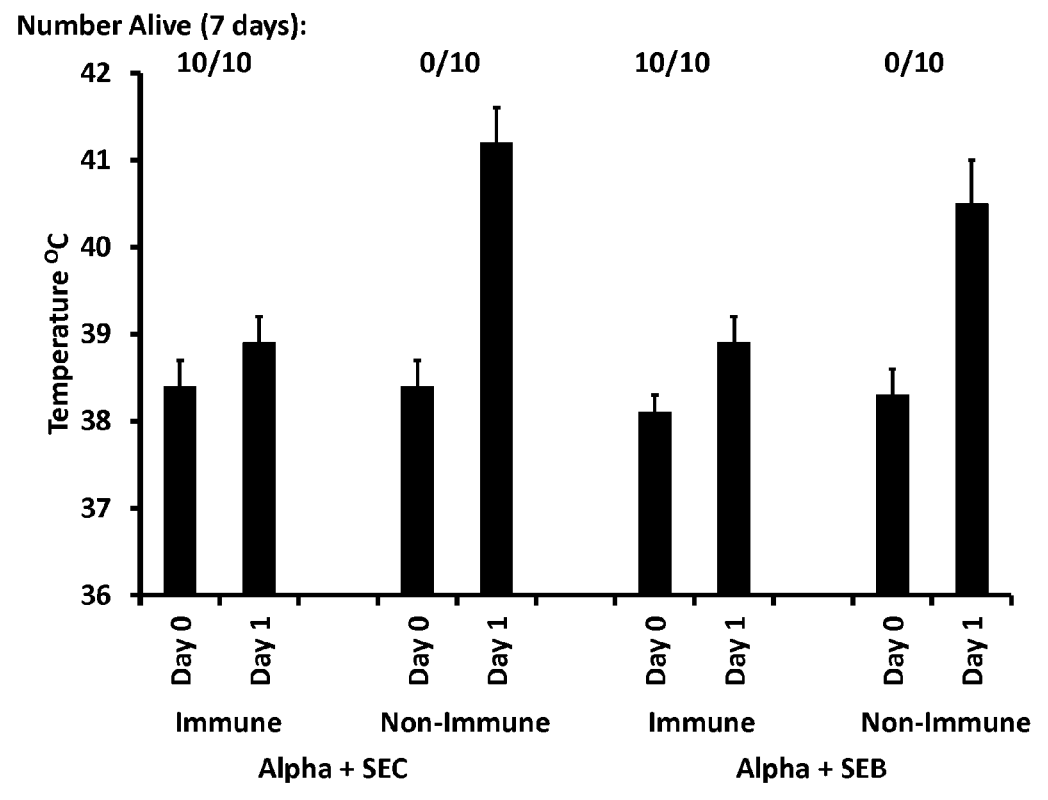

The results of the experiment are shown in FIG. 13. Animals (New Zealand white rabbits, either sex, 2-3 Kg) showed rises in body temperatures when day 0 (pre-infection) was compared to day 1 post infection. The rises in body temperatures in non-immune animals were significantly higher than in immunized animals on day 1 ($P \ll 0.001$) as tested by Student's t test analysis. The data show that immunity to alpha toxin and the respective superantigens protects significantly against fever development. Non-immune animals in both groups challenged with either CAMRSA strain uniformly succumbed by day 3 post-infection. All had hemorrhagic necrotizing pneumonia. In contrast, none of the immune animals succumbed, and indeed, all appeared healthy on day 7 post-infection. The survival difference between immune and non-immune animals was significant a $P < 0.0001$ for both challenge organism by Fisher's exact test. These data indicate that immunity to alpha toxin and the major superantigen (SEB or SEC) produced by USA400 CA-MRSA protects from necrotizing pneumonia.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising two or more staphylococcal toxoids, said composition comprising:
   (a) at least one toxoid selected from the group consisting of a staphylococcal enterotoxin-like X (SEL-X) toxoid, an alpha toxin toxoid, a beta toxin toxoid, and a gamma toxin toxoid; and
   (b) at least one toxoid selected from the group consisting of a toxic shock syndrome toxin-1 (TSST-1) toxoid, a staphylococcal enterotoxin B (SEB) toxoid comprising SEQ ID NO:3 but having one or more of the following: a threonine at position 20, an alanine residue at position 90, a valine residue at position 91, or an alanine residue at position 210, and a staphylococcal enterotoxin C (SEC) toxoid.

2. The composition of claim 1, wherein said TSST-1 toxoid comprises SEQ ID NO:1 but having a serine residue at position 31 and a proline residue at position 32; wherein said TSST-1 toxoid is a fusion protein; wherein said TSST-1 toxoid comprises SEQ ID NO:1 but having an alanine residue at position 135 or an alanine at position 136; or wherein said TSST-1 toxoid comprises SEQ ID NO:1 but having a glutamine at position 139.

3. The composition of claim 1, wherein said SEB toxoid comprises SEQ ID NO:3 but having an alanine residue at position 90 and an alanine residue at position 210.

4. The composition of claim 1, wherein said SEC toxoid is a SEC3 toxoid.

5. The composition of claim 1, wherein said composition comprises three, four, or five staphylococcal toxoids.

6. The composition of claim 1, wherein said composition comprises a TSST-1 toxoid, a SEB toxoid, a SEC toxoid, an alpha toxin toxoid, and a beta toxin toxoid.

7. The composition of claim 6, said composition further comprising a SEL-X toxoid and/or a gamma toxin toxoid.

8. The composition of claim 7, wherein said gamma toxin toxoid is a single chain of the gamma *Staphylococcus* toxin.

9. The composition of claim 8, wherein said single chain is the B chain of the gamma *Staphylococcus* toxin.

10. The composition of claim 1, wherein said composition comprises a SEC toxoid, a SEB toxoid, and an alpha toxin toxoid.

11. The composition of claim 1, said composition further comprising an adjuvant.

12. A composition comprising a) a TSST-1 toxoid, a SEC toxoid, a staphylococcal alpha toxin toxoid, a staphylococcal beta toxin toxoid, and a gamma toxin toxoid, or b) a TSST-1 toxoid, a SEC toxoid, and a staphylococcal alpha toxin toxoid.

13. The composition of claim 12, wherein each of combination (a) and (b) further comprises a SEB toxoid.

14. The composition of claim 12, wherein each of combination (a) and (b) further comprises an adjuvant.

15. The composition of claim 1, wherein said composition comprises said gamma toxin toxoid, and wherein said gamma toxin toxoid comprises:
   a single polypeptide chain of a gamma toxin, wherein said single polypeptide chain is immunogenic but not toxic.

16. The composition of claim 1, wherein said SEC toxoid comprises SEQ ID NO:2 but having an alanine residue at position 90 and/or an alanine residue at position 210.

17. The composition of claim 1, wherein said alpha toxin toxoid comprises SEQ ID NO:5 but having a leucine residue at position 35.

18. The composition of claim 1, wherein said beta toxin toxoid comprises SEQ ID NO:6 but having an asparagine at position 149 and/or an asparagine at position 288.

* * * * *